US012377066B2

(12) United States Patent
Panasyuk et al.

(10) Patent No.: US 12,377,066 B2
(45) Date of Patent: Aug. 5, 2025

(54) TREATMENT OF DISEASES ASSOCIATED WITH BILIARY SYSTEM DESTRUCTION

(71) Applicants: Assistance Publique-Hopitaux de Paris, Paris (FR); Centre National De La Recherche Scientifique, Paris (FR); Institut National de la Santé et de la Recherche Médicale, Paris (FR); Université de Paris, Paris (FR)

(72) Inventors: Ganna Panasyuk, Paris (FR); Muriel Girard, Issy les Moulineaux (FR)

(73) Assignees: Assistance Publique-Hopitaux de Paris, Paris (FR); Centre National De La Recherche Scientifique, Paris (FR); Institut National de la Santé et de la Recherche Médicale, Paris (FR); Université de Paris, Paris (FR)

( * ) Notice: Subject to any disclaimer, the term of this patent is extended or adjusted under 35 U.S.C. 154(b) by 1017 days.

(21) Appl. No.: 17/283,843

(22) PCT Filed: Oct. 11, 2019

(86) PCT No.: PCT/EP2019/077668
§ 371 (c)(1),
(2) Date: Apr. 8, 2021

(87) PCT Pub. No.: WO2020/074737
PCT Pub. Date: Apr. 16, 2020

(65) Prior Publication Data
US 2021/0379003 A1  Dec. 9, 2021

(30) Foreign Application Priority Data
Oct. 11, 2018 (EP) .................................. 18306343

(51) Int. Cl.
*A61K 31/216* (2006.01)
*A61K 9/00* (2006.01)
*A61K 31/195* (2006.01)
*A61P 1/16* (2006.01)

(52) U.S. Cl.
CPC .......... *A61K 31/216* (2013.01); *A61K 31/195* (2013.01); *A61P 1/16* (2018.01); *A61K 9/0053* (2013.01)

(58) Field of Classification Search
CPC .. A61K 31/195; A61K 31/192; A61K 31/455; A61K 31/216
USPC .................. 514/356, 533, 534, 543
See application file for complete search history.

(56) References Cited

U.S. PATENT DOCUMENTS

2009/0111782 A1* 4/2009 De Bosscher ......... A61K 31/44
514/369

FOREIGN PATENT DOCUMENTS

WO  2007053622 A2  5/2007
WO  2017167935 A1  10/2017

OTHER PUBLICATIONS

Tyraskis, et al., Cochrane Database Syst. Rev. May 14, 2018;(5); pp. 1-34. (Year: 2018).*
Bezerra, et al. "Biliary Atresia: Clinical and Research Challenges for the Twenty-First Century." Hepatology. Vol. 68. No. 3. Sep. 2018. pp. 1163-1173.
International Search Report & Written Opinion in PCT/EP2019/077668 dated Feb. 14, 2020, 9 pages.
Girard, et al. "Biliary atresia: does ethnicity matter?" Journal of Hepatology. 2012. vol. 57. pp. 699-711.
Diem, et al. "Pediatric Liver Transplantation for Biliary Atresia: Results of Primary Grafts In 328 Recipients." Transplantation. May 27, 2003. vol. 75, No. 10. pp. 1692-1697.
Fischler, et al. "Cholestasis in the newborn and infant." Clinics and Research in Hepatology and Gastroenterology (2014) vol. 38. pp. 263-267.
Serinet, et al. "Impact of Age at Kasai Operation on Its Results in Late Childhood and Adolescence: A Rational Basis for Biliary Atresia Screening." Official Journal of the American Academy of Pediatrics 2009. vol. 123. pp. 1280-1286.
Fouquet, et al. "Long-Term Outcome of Pediatric Liver Transplantation for Biliary Atresia: A 10-Year Follow-Up in a Single Center." Liver Transplantation, vol. 11, No. 2 (Feb.), 2005. pp. 152-160.
Hübscher, Stefan G. "What is the long-term outcome of the liver allograft?" Journal of Hepatology 2011. vol. 55. pp. 702-717.
Bezerra, et al. "Use of Corticosteroids After Hepatoportoenterostomy for Bile Drainage in Infants With Biliary Atresia: The START Randomized Clinical Trial." JAMA. 2014. May 7, 2014. vol. 311. No. 17. pp. 1750-1759.
Willot, et al. "Effect of Ursodeoxycholic Acid on Liver Function in Children After Successful Surgery for Biliary Atresia." Official Journal of the American Academy of Pediatrics 2008. Volume 122, No. 6, Dec. 2008. pp. 1236-1241.
Nizery, et al. "Biliary atresia: Clinical advances and perspectives." Clinics and Research in Hepatology and Gastroenterology. Jan. 5, 2016. vol. 40. pp. 281-287.

(Continued)

*Primary Examiner* — Jeffrey H Murray
*Assistant Examiner* — Luisalberto Gonzalez

(57) ABSTRACT

The present invention relates to the field of neonatal cholestasis, in particular the treatment of neonatal biliary atresia or diseases associated with biliary system destruction. Also, the invention relates to methods and/or compounds for treating or preventing biliary atresia or disease associated with biliary system destruction. It further relates to methods and/or compounds for slowing the progression of biliary atresia or disease associated with biliary system destruction.

14 Claims, 12 Drawing Sheets

(56) References Cited

OTHER PUBLICATIONS

Davenport, et al. "Steroids in biliary atresia: Single surgeon, single centre, prospective study." Journal of Hepatology. 2013. vol. 59. pp. 1054-1058.
Chen, et al. "Postoperative steroid therapy for biliary atresia: Systematic review and meta-analysis." Journal of Pediatric Surgery. 2015. vol. 50. pp. 1590-1594.
Chardot, et al. "Improving outcomes of biliary atresia: French national series 1986-2009." Journal of Hepatology. 2013. vol. 58. pp. 1209-1217.
Chardot, et al. "Epidemiology of biliary atresia in France: a national study 1986-96." Journal of Hepatology. 1999. vol. 31. pp. 1006-1013.

\* cited by examiner

TREATMENT OF DISEASES ASSOCIATED WITH BILIARY SYSTEM DESTRUCTION

TECHNICAL FIELD

The present invention relates to the field of neonatal cholestasis, in particular the treatment of neonatal biliary atresia or diseases associated with biliary system destruction. The invention relates to methods and/or compounds for treating or preventing biliary atresia or disease associated with biliary system destruction or for slowing the progression of biliary atresia or disease associated with biliary system destruction.

BACKGROUND ART

Biliary atresia (BA) is a rare disease characterized by a severe inflammatory obliterative cholangiopathy that affects both extrahepatic and intrahepatic bile ducts. The obstruction of biliary ducts appears in the perinatal period. The incidence in the world varies between 1/20,000 and 1/5,200 live births, Asia and the Pacific countries being the most affected, in particular French Polynesia (Girard M et al. Biliary atresia: does ethnicity matter? J Hepatol 2012; 57:700-1). Its incidence in Europe is 1/18,000 live births (Chardot C et al. Epidemiology of biliary atresia in France: a national study 1986-96. J Hepatol 1999; 31:1006-13) and it is the first indication of hepatic transplantation in children (Diem H V et al. Pediatric liver transplantation for biliary atresia: results of primary grafts in 328 recipients. Transplantation 2003; 75:1692-7)

BA symptoms occur shortly after birth. The typical clinical triad of BA is jaundice (due to bilirubin going through the blood), acholic stools and hepatomegaly. The diagnosis is made after a complete clinical examination and the exclusion of other main causes of neonatal cholestasis (Fischler B, Lamireau T. Cholestasis in the newborn and infant. Clin Res Hepatol Gastroenterol 2014; 38:263-7). Clinical histopathological analyses reveal intra- and extrahepatic biliary duct obstruction, progressive fibrosis and inflammation. In most of the cases (80%), bile duct alteration is isolated, however, "syndromic" forms are also observed in 20% of cases. In this case, bile duct alterations are associated with other organ malformations or with heterotaxia (abnormal laterality determination), indicating embryonic problem with antenatal onset. For some patients, (30-50% of the total cohorts) histological analysis identified ductal plate malformation: foetal form of bile duct organization in the portal tracts. Until now, the causes of BA and its pathophysiological mechanism remain unknown. BA is the first cause of neonatal cholestasis and the first indication of liver transplant in children (Chardot C et al. Improving outcomes of biliary atresia: French national series 1986-2009. J Hepatol 2013; 58:1209-17).

Treatment of BA remains very limited. Untreated, BA leads to a liver failure and a death in the first years of life. In a first phase, to restore biliary flow between liver and intestine, Kasai operation (resection of the obstructed extrahepatic bile ducts) will be performed in neonatal period (Serinet M O et al. Impact of age at Kasai operation on its results in late childhood and adolescence: a rational basis for biliary atresia screening. Pediatrics 2009; 123:1280-6). This surgical procedure leads to a restauration of the bile flow for 50% of patients. But with time, it is mostly transient and, in case of failure (initial or secondary), will be followed by a liver transplantation. At the end, 75% to 80% of BA patients would require a liver transplantation.

The prognosis of BA has dramatically changed in the last decades: before the Kasai operation most BA patients died, while, nowadays, with the sequential treatment with Kasai operation and/or liver transplantation BA patient's survival is close to 90% (Fouquet V et al. Long-term outcome of pediatric liver trans-plantation for biliary atresia: a 10-year follow-up in a single center. Liver Transpl 2005; 11:152-60; Hubscher. What is the long-term outcome of the liver allograft? J Hepatol 2011; 55:702-17). Early diagnosis is very important since the chances of success in restoring the bile flow after the Kasai procedure decrease with time (Serinet M O et al. Impact of age at Kasai operation on its results in late childhood and adolescence: a rational basis for biliary atresia screening. Pediatrics 2009; 123:1280-6).

The pathological mechanisms of BA remain unknown but several mechanisms including genetic and immune dysregulation were proposed to contribute to the obliterative cholangiopathy. Current research focuses on the identification of blood or liver factors linked to the pathogenesis of BA that could become therapeutic targets and avoid or postpone the need for liver transplantation (Nizery L et al. Biliary atresia: Clinical advances and perspectives. Clin Res Hepatol Gastroenterol. 2016 June; 40(3):281-287). No similar disease leading to total obstruction of the biliary tree exists in older children or adults. However, the understanding of physiopathology of BA may highlight the mechanisms of other destructive cholangiopathies, such as sclerosing cholangitis.

In the past, BA patients were treated with corticoids just after the Kasai operation. This was done in hope to stop inflammation in the bile ducts. However, a recent study reported that this treatment does not affect the outcomes of Kasai operation neither at early nor at long term. It also does not change the long-term prognosis of patients (in terms of survival) (Davenport M et al. Steroids in biliary atresia: single surgeon, single centre, prospective study. J Hepatol 2013; 59:1054-8; Chen Y, et al. Postoperative steroid therapy for biliary atresia: systematic review and meta-analysis. J Pediatr Surg 2015; 50:1590-4). Furthermore, the corticoid treatment could cause side effects such as infection or surgical complications just after the Kasai operation (Bezerra J A et al. Use of corticosteroids after hepatoportoenterostomy for bile drainage in infants with biliary atresia: the START randomized clinical trial. JAMA 2014; 311:1750-9).

Alternately, another medication used in clinic is UDCA (desoxycholic acid). It is a bile acid expected to make bile more hydrophilic and so to improve the bile drainage. Furthermore, it was suggested to have immunomodulation effect. However, no controlled studies were performed to prove the therapeutic benefits of this molecule and the large use of this treatment during many years provided no evidence that it might positively affect prognosis of the patients in term of % of liver transplantation or survival (Willot S et al. Effect of ursodeoxycholic acid on liver function in children after successful surgery for biliary atresia. Pediatrics 2008; 122:e1236-41)

Currently, there is no pharmacological treatment that would have been shown to have a beneficial effect in BA. Kasai intervention is the unique treatment that can be proposed in the first step, but it is a heavy surgery for neonatal patients and only successful in 50% of patients. Thus, there is a need for compounds or methods for treating neonatal biliary atresia or diseases associated with biliary system destruction (Nizery L et al. Biliary atresia: Clinical advances and perspectives. Clin Res Hepatol Gastroenterol. 2016 June; 40(3):281-287).

SUMMARY OF THE INVENTION

In the context of the present invention, the inventors surprisingly found that fibrate compounds can be used in the treatment of biliary atresia or disease associated with biliary system destruction and/or the prevention and/or slow down the progression of biliary atresia.

The inventors have discovered that hepatic mutant of regulatory subunit of the class 3 PI3K, Vps15 (Vps15 LKO) presented hepatomegaly and intrahepatic bile system disruption with the histological findings highly reminiscent of clinical manifestation in BA patients. The inventors demonstrated that Vps15 deletion in liver results in accumulation of p62, LC3 and lysosomal proteins such as Lamp1 and 2, showing a profound deregulation of lysosomal clearance by autophagic pathway. Unexpectedly, they found that an inhibition of the class 3 PI3K signaling in hepatocytes manifested in mitochondrial depletion and failure to oxidize fatty acids.

The macroautophagy (thereafter referred as autophagy) is a catabolic process for lysosomal degradation of the intracellular components. Autophagy is essential for cellular homeostasis and integrity, and conserved from the yeast to humans. The principal feature of autophagy is a formation of double-membrane vesicles (autophagosomes) that enclose cytoplasmic components targeted for lysosomal destruction. Autophagy takes place in different steps and is tightly regulated on a molecular level. The initiation and recruitment of membrane sources to form the double membrane cap (phagophore) requires the activity of three enzymatic complexes: mTOR (mechanistic Target of Rapamycine Complex) acting upstream of ULK (UNC-51-like Kinases) and the class 3 PI3K (phosphoinositide 3-kinase). The phagophore membrane will then elongate thanks to different ATG genes (AuTophaGy related genes) including ATGS/ATG12 complex and LC3-II in order to sequester material to degrade. In a process of maturation, LC3 protein is modified by conjugation with phosphatidylethanolamine giving LC3-II form. Finally, autophagosome fuses with lysosome containing acidic hydrolases that will allow degradation of autophagosome content. Although autophagy serves as a pathway for a bulk degradation, its selectivity is assured by receptor proteins that recognise and bind cargoes destined to a destruction. One of these actors is p62 receptor or SQSTM-1 protein. It contains a protein recognition domain for ubiquitin and LC3 interaction domain.

The class 3 PI3K has a central evolutionarily conserved role in coordination of vesicular trafficking, endocytosis and autophagy in response to nutrient availability. It is present in every eukaryotic cell, from yeast, in which it was initially discovered, to mammals. The catalytically active the class 3 PI3K complex is formed by the catalytic Vps34 and the regulatory Vps15 subunits. Vps15 is a putative serine/threonine protein kinase, which is required for Vps34 stability, activity and membrane targeting. The lipid kinase activity of Vps34 is a major source of phosphatidylinositol 3-phosphate (PI3P) in the cell, which functions as secondary messenger at the intracellular membranes and docking signal for proteins containing PI3P-binding domains. During autophagy initiation, PI3P is generated at phagophore membrane. Binding to PI3P promotes the formation of protein scaffolds that are involved in the autophagic membrane extension. Importantly, it also promotes membrane fusion of the autophagosome with the lysosome. Finally, PI3P is required for endocytic trafficking from the plasma membrane towards the lysosome, endosomal sorting of the cargos destined to the degradation and for the lysosomal delivery of the hydrolases. Therefore, class 3 PI3K has a central role in cellular trafficking and catabolic metabolism. Class 3 PI3K contributes to these pleiotropic functions by engaging distinct protein complexes which are formed by recruitment of accessory subunits to the core Vps15/Vps34 complex. To this end, a binding of Atg14-related protein (ATG14) or ultraviolet radiation resistance-associated gene protein (UVRAG) to a Vps34/Vps15 complex is mutually exclusive. ATG14-containing complex stimulates Vps34 activity at the phagophore membranes and is required for autophagy initiation in response to nutrient withdrawal. The UVRAG-containing complex is implicated in endosome and autophagosome maturation. In addition to Vps15/Vps34, both complexes have in common the presence of Beclin-1 protein, which promotes lipid kinase activity of Vps34.

Unexpectedly, inventors show that nuclear expression and activity of nuclear receptor transcription factor Peroxisome Proliferator Activated Receptor alpha (PPARα) is decreased in liver tissue of Vps15-LKO mouse. PPARα is a transcription factor nutrient sensor that is activated by binding of fatty acids and its activity in hepatocytes assures the activation of genes required for fatty acid oxidation (FAO) as well as autophagy.

Surprisingly, the inventors found that pharmacologic activation of PPARα by fibrate compounds that are synthetic ligands of PPARα, in particular fenofibrate and/or bezafibrate, restored lipid oxidation in liver tissue of Vps15 LKO mice. Also, the inventors found that the administration of fenofibrate and/or bezafibrate, ameliorated the liver functions and restored autophagic flux in the liver of Vps15 LKO mice.

Finally, the inventors show that autophagy is blocked in livers of BA patients. To reach this affirmation, inventors studied 30 liver biopsies of BA patients and observed that 30% of patients showed a 50% decrease in the protein expression of the class 3 PI3K subunits including core subunits Vps15, Vps34 and Beclin-1 protein. Furthermore, the immunohistological analyses in liver tissue of BA patients demonstrated an accumulation of p62 and Lamp1 proteins showing the autophagy block.

In a first aspect, the present invention thus relates to fibrate compounds for its use in the treatment or prevention of biliary atresia or disease associated with biliary system destruction.

The invention further relates to a fibrate compound for its use in slowing the progression of biliary atresia or disease associated with biliary system destruction.

In a preferred embodiment, the fibrate compound is an agonist of the alpha form of PPAR (PPARα). In another preferred embodiment, the fibrate compound is an agonist of the alpha form of PPAR (PPARα) except the elafibranor.

The fibrate compound is chosen from the group consisting in fenofibrate, ciprofibrate, gemfibrozil, bezafibrate, clinofibrate, clofibrate, clofibride, ronifibrate and simfibrate, more preferably, fenofibrate or bezafibrate. Particularly, the fibrate compound is chosen from the group consisting in fenofibrate, ciprofibrate, bezafibrate, clinofibrate, clofibrate, clofibride, ronifibrate and simfibrate.

The invention also relates to a combination of fibrate compounds. For example, the invention also relates to a combination of bezafibrate and fenofibrate for its use in the treatment of biliary atresia.

Advantageously, fibrate compound is administered to a subject or a patient suffering from biliary atresia or disease associated with biliary system destruction, in particular the subject or the patient is a neonate, an infant or a child.

In another embodiment, biliary atresia is treated surgically. Neonate, or infant suffering from biliary atresia with biliary system destruction is treated by a Kasai portoenterostomy surgery to restore the bile flow to the intestine. This surgery permits to restore bile flow in 50% of patients while for other 50% of patients the Kasai surgery fails to restore bile flow because of the alteration of intrahepatic bile ducts. Notably, some patients who initially underwent a successful Kasai surgery will become secondarily jaundice because of continuous alteration of intrahepatic bile ducts. Accordingly, the treatment of the present invention is advantageously administered after a Kasai portoenterostomy surgery.

In a second aspect, the invention relates to compounds for its use in the prevention or slowdown the progression of biliary atresia or disease associated with biliary system destruction, in the form of a pharmaceutical composition. The term "prevention" means to prevent the destruction of biliary ducts and/or slowdown of the progression of the intra hepatic lesions.

As for samples, on the left: "Control" is a non-BA patient (n=8, including patient samples of non-tumoral liver tissue of liver adenoma patients, methyl malonic acidemia, oxalosis, neonatal sclerosis cholangitis and healthy liver donor tissue sample). These sample type showed weak/no positive staining for p62 and Lamp1 protein, therefore suggesting that autophagy pathway is intact.

"BA patient #1 and #2" liver samples of BA patients (analyzed n=14 patients). "BA patient #1" is a representative image of analyses in liver samples collected at the time of the liver transplantation (infant patients, 6 months to 2 years old) for the children who have failed Kasai operation. "BA patient #2" is a representative image of analyses in liver samples collected at the time of Kasai operation (neonatal period: 1 or 2 months of age).

Analyses in both sample groups of BA patients show marked p62 staining in the hepatocytes around the portal tracks with granular staining of p62 that accumulates in the cytoplasm of hepatocytes. In addition to hepatocytes, the positive p62 staining is observed in the cholangiocytes of bile ducts both in remnants near the portal tracks and in proliferating bile ducts.

The table presented below the histological captures summarizes the histological analyses performed on the ensemble of patient liver tissue samples. Labelling P62−, p62+ and p62++ corresponds to weak, moderate and high positive staining, respectively. In total, p62 protein accumulation is observed in 12 out of 14 patients liver sample collected at the time of transplantation and Kasai operation. Lamp1 protein accumulation is observed in 8 out of 8 patients liver sample collected at the time of transplantation and Kasai operation. These observations show defective autophagy process both in hepatocytes and cholangiocytes in liver tissue of the BA patients compared to controls.

Figure 2:
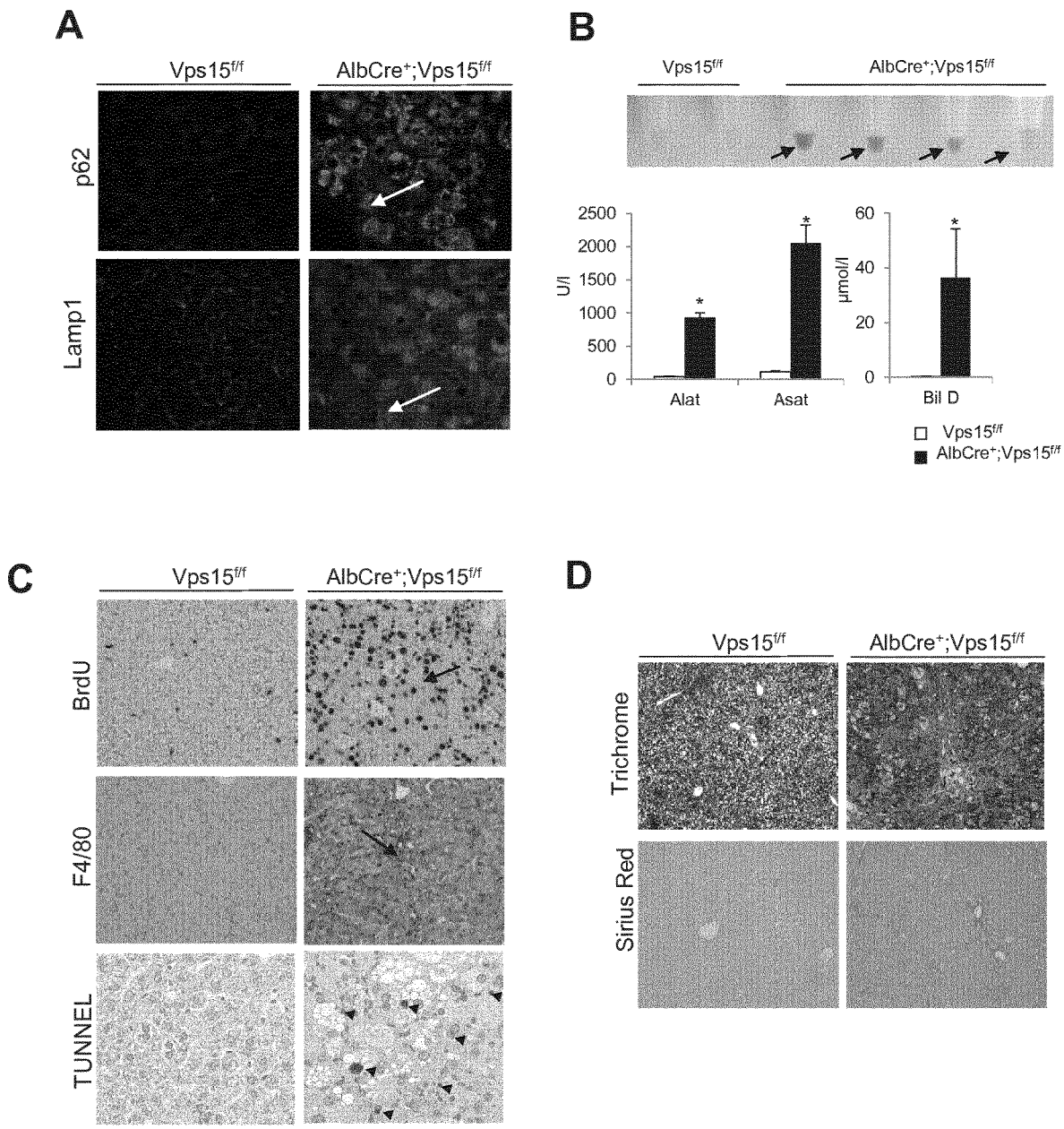

FIG. 2 represents images of histological and plasma analyses in Vps15LKO mice. FIG. 2A. Immunohistochemistry with anti-p62 and anti-Lamp1 antibodies of liver tissue slices of control and Vps15LKO mice show important accumulation of both proteins in livers of mutant mice. FIG. 2B. Image capture of tubes with plasma of control and Vps15LKO mice showing grey color (arrow) of plasma from Vps15LKO animals that signifies important bilirubin content. The graph panels below show the significantly increased plasmatic levels of hepatic transaminases (Alat, Asat) and plasmatic bilirubin level (Bil D) in Vps15LKO mice. FIG. 2C. immunohistological analyses in control and Vps15LKO mice showing increased proliferation, immune cell infiltration and apoptosis revealed by BrdU labelling, F4/80 antigen immunohistochemistry and positive Tunel staining in livers of Vps15LKO animals (arrow). FIG. 2D. Histological analyses with Trichrome and Sirius red staining in liver slices of control and Vps15LKO mice showing significant fibrotic deposits in Vps15 mutants.

Figure 1:
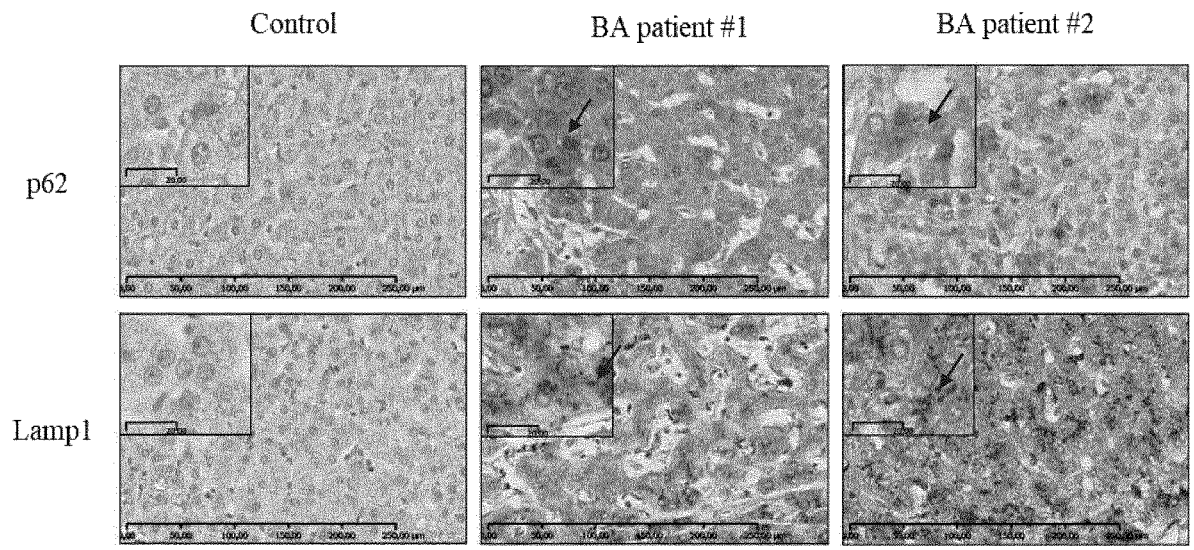
FIG. 1 represents an image of immunohistochemical analyses of liver tissue using anti-p62 and anti-Lamp1 antibodies. p62 protein levels are used in this case as a read-out of autophagy status as this protein is degraded in lysosomes through autophagy pathway. Lamp1 is a lysosomal membrane protein, therefore, it is used in this assay to assess the lysosomal mass. In case of defective autophagy, p62 protein level is accumulated. Both cytosolic and nuclear accumulation of p62 protein were reported. In case of defective autophagy, accumulation of Lamp1 is suggestive of dysfunctional lysosomal hydrolytic activity. The positive staining of p62 and Lamp1 proteins in hepatocytes and cholangiocytes seen as accumulation of brown deposit (arrow) reflecting higher protein levels.
Figure 3:
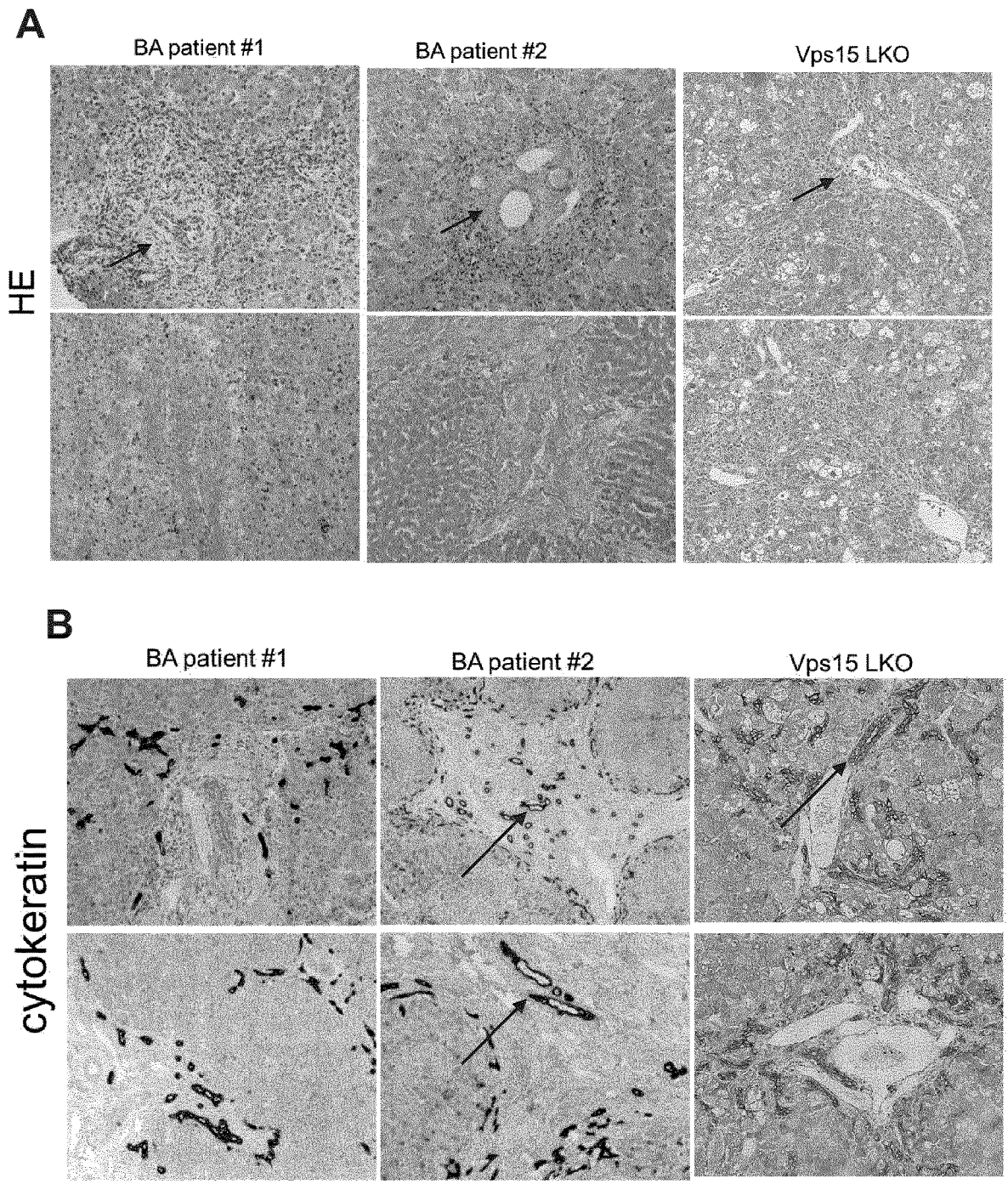

FIG. 3 is a representative image of gross microscopic liver structure (FIG. 3A) and immunohistochemistry with anti-pan-cytokeratin antibody (FIG. 3B) of Vps15LKO mutant and liver biopsy of biliary atresia patients of two groups defined as in FIG. 1. FIG. 3A. Hematoxylin/eosin staining of liver tissue samples shows altered liver structure with portal fibrosis, ballooned hepatocytes, cholestasis, and biliary proliferation in the portal tracts (arrows). FIG. 3B. Positive pan-cytokeratin staining shows the biliary duct proliferation (arrows) both in BA patients and in livers of Vps15LKO mice. These analyses show that inactivation of the class 3 PI3K in liver manifests in the intrahepatic alterations similar to the pathological features observed in BA patients.

Figure 4:
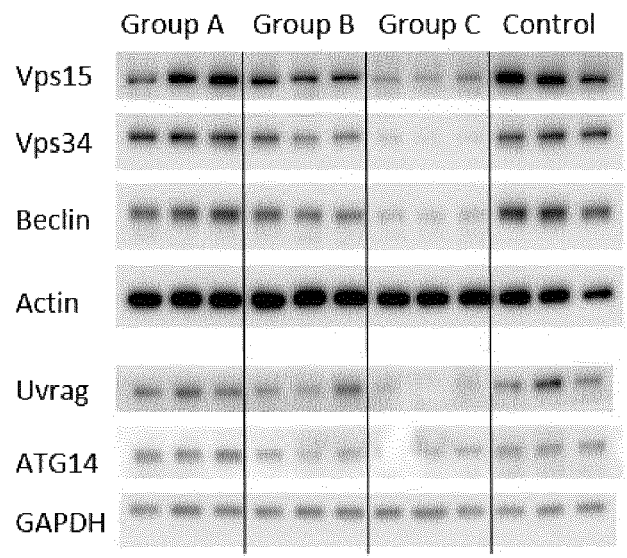
Figure 4:
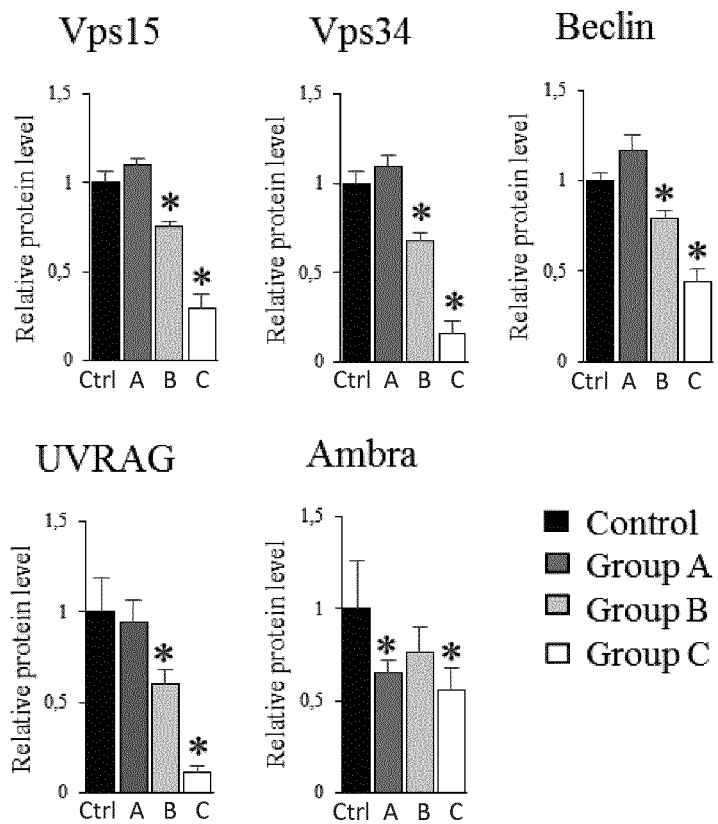

FIG. 4 represents immunoblot analyses (FIG. 4A) and its quantification (FIG. 4B) to evaluate the expression levels of the class 3 PI3K subunits (Vps15, Vps34, Beclin, UVRAG, Atg14L) in liver tissue of BA patients (n=30). The immunoblot with anti-actin and anti-GAPDH served as a loading control. These analyses demonstrated presence of three expression groups. Group A (n=12): expression of all subunits including core subunits in the complex such as Vps15, Vps34 and Beclin is the same as in controls. Group B (n=10), expression of the core subunits in the complex is significantly lower (by 30%) compared to controls. Group C (n=8), expression of the core subunits in the complex is significantly depleted (over 50%) of all subunits compared to controls. Controls are the liver tissue samples of healthy liver tissue (transplantation donor) and patients with disease non-related to BA. These analyses show that expression of the class 3 PI3K subunits is decreased in liver tissue of a large proportion of BA patients.

Figure 5:
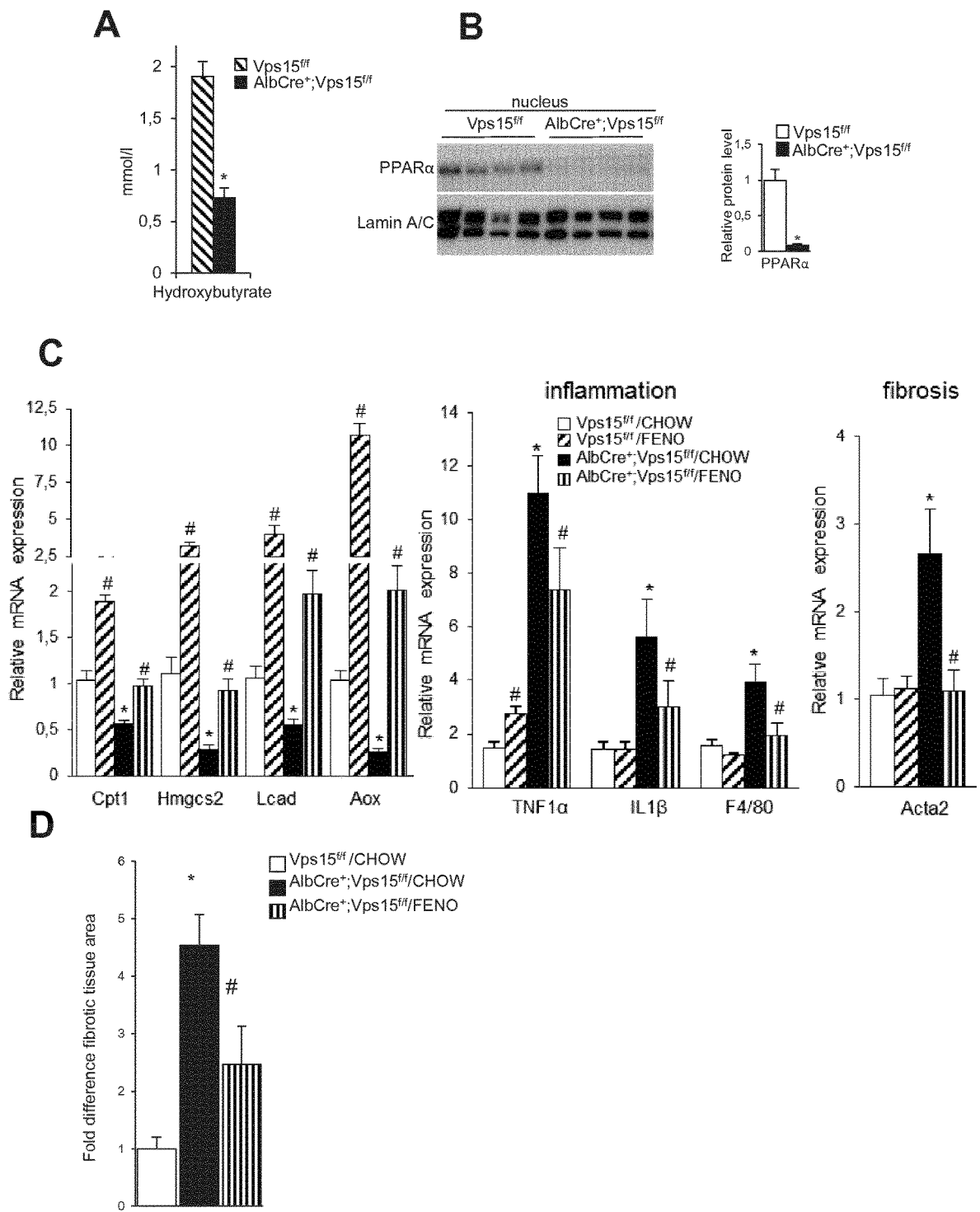

FIG. 5 represents the analyses in Vps15LKO mutants that demonstrate defective PPARα function. FIG. 5A Graph shows that plasmatic levels of ketone body hydroxybutyrate is significantly decreased in plasma of fasted Vps15LKO mutants. FIG. 5B. Immunoblot analyses and its quantification of nuclear protein liver extracts of random-fed six week old control (Vps15f/f) and Vps15LKO mutant (AlbCre+; Vps15f/f) using antibodies specific to PPARα. Immunoblot with LaminA/C antibody served as a loading control. Densitometric analyses of protein levels normalised to LaminA/C levels presented as folds over Vps15f/f-chow condition. Data are means±SEM (n=4 for Vps15f/f, n=6 for AlbCre+; Vps15f/f, P<0.05*: vs Vps15f/f, 2-tailed, unpaired Student's t test). FIG. 5C. Transcript level analyses in liver tissue samples showing the restoration of PPARα function by fenofibrate treatment in Vps15LKO mice. Relative transcript levels of metabolic enzymes in ketogenesis (HMGCS2), FAO (CPT1, LCAD, AOX), inflammation (TNF1α, IL1β, F4/80) and fibrosis (Acta2) in livers of fed control and Vps15LKO mice that were treated for two weeks with fenofibrate. Data are means±SEM (Vps15f/f (n=6 and n=4 for chow and FENO group), AlbCre+; Vps15f/f (n=5 and n=4 for chow and FENO group), $P<0.05$*: vs Vps15f/f, # vs chow, 2-tailed, unpaired Student's t test). Altogether, these analyses show that PPARα transcriptional activity is inhibited in livers of Vps15LKO mice. FIG. 5D. Graph shows that significantly increased fibrosis observed in livers of Vps15 LKO mice is decreased by fenofibrate treatment. Sirius Red staining as a measure of fibrosis was performed on liver tissue samples of fed control and Vps15LKO mice that were treated for two weeks with fenofibrate. The relative accumulation of Sirius Red positive signal was quantified using CaloPix image tool software.

Figure 6:
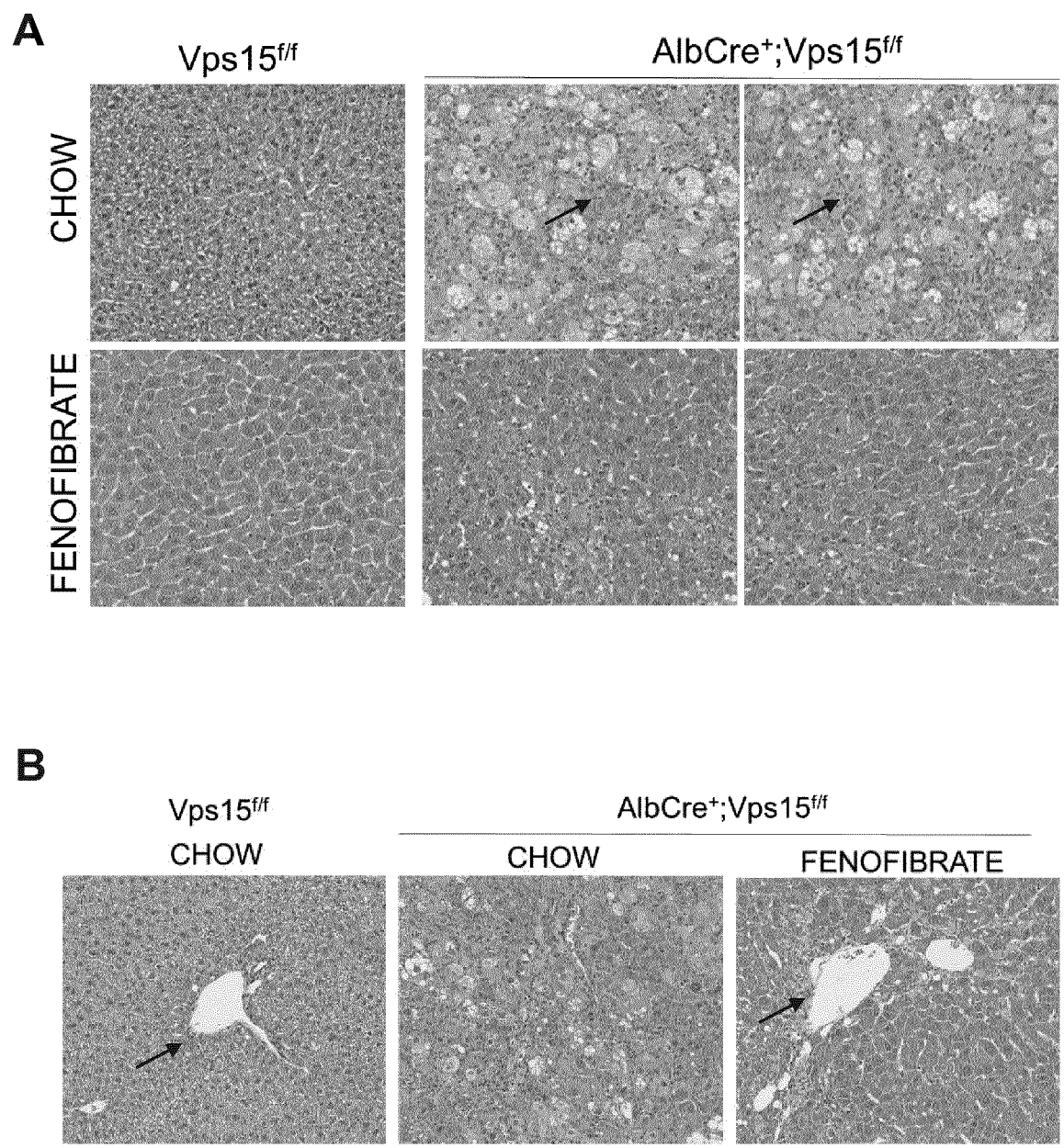

FIG. 6 represents the histological analyses of liver tissue in control and Vps15LKO mice that were treated for short-term with fenofibrate. Mice at the age of 5 weeks were treated for 2 weeks with fenofibrate at the dose 200 mg/kg/day. Fenofibrate was incorporated in food. Its efficacy for PPARα activation was confirmed by positive transcriptional responses as seen on FIG. 5C. Representative images of hematoxylin/eosin staining of formol fixed paraffin embedded liver tissue of control and fenofibrate treated mice are presented for lobular area (FIG. 6A) and portal area (FIG. 6B). Those show that pharmacological activation of PPARα by fenofibrate rescues hepatocyte vacuolation (FIG. 6A) and ameliorates architecture of biliary system (FIG. 6B) in Vps15LKO mice. These analyses show that re-activation of PPARα in Vps15 LKO mice results in significant amelioration of liver architecture.

Figure 7:
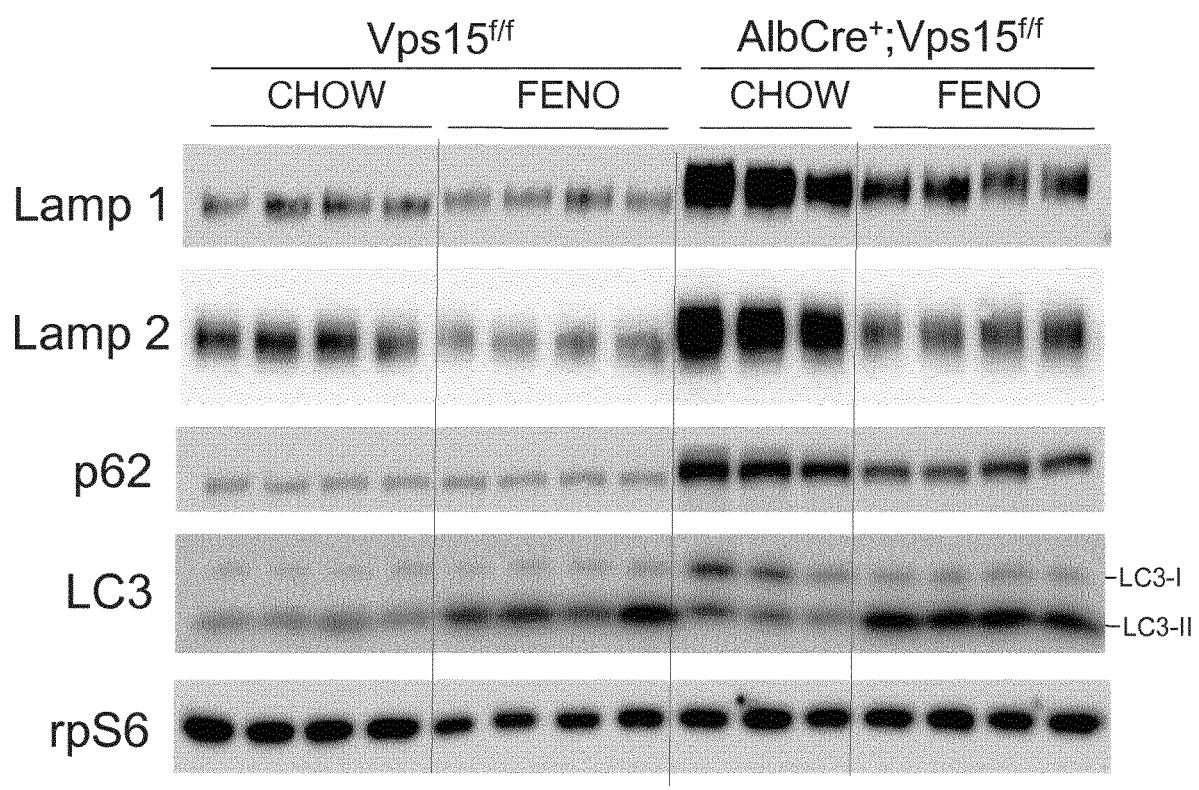

FIG. 7 represents immunoblot analyses of total protein liver extracts of mice treated as in FIG. 6 with indicated antibodies. Immunoblot with rpS6 antibody served as a loading control. Immunoblot with anti-Lamp1 and anti-Lamp2 antibodies shows that accumulation of these proteins in livers of Vps15 mutants is significantly reverted by fenofibrate treatment. In the same way, fenofibrate treatment decreased levels of p62 protein in livers of Vps15LKO mice. Importantly, fenofibrate treatment promoted LC3-lipidation both in control and in livers of Vps15LKO mice. These analyses show that PPARα re-activation in livers of Vps15LKO mice promotes autophagic clearance.

Figure 8:
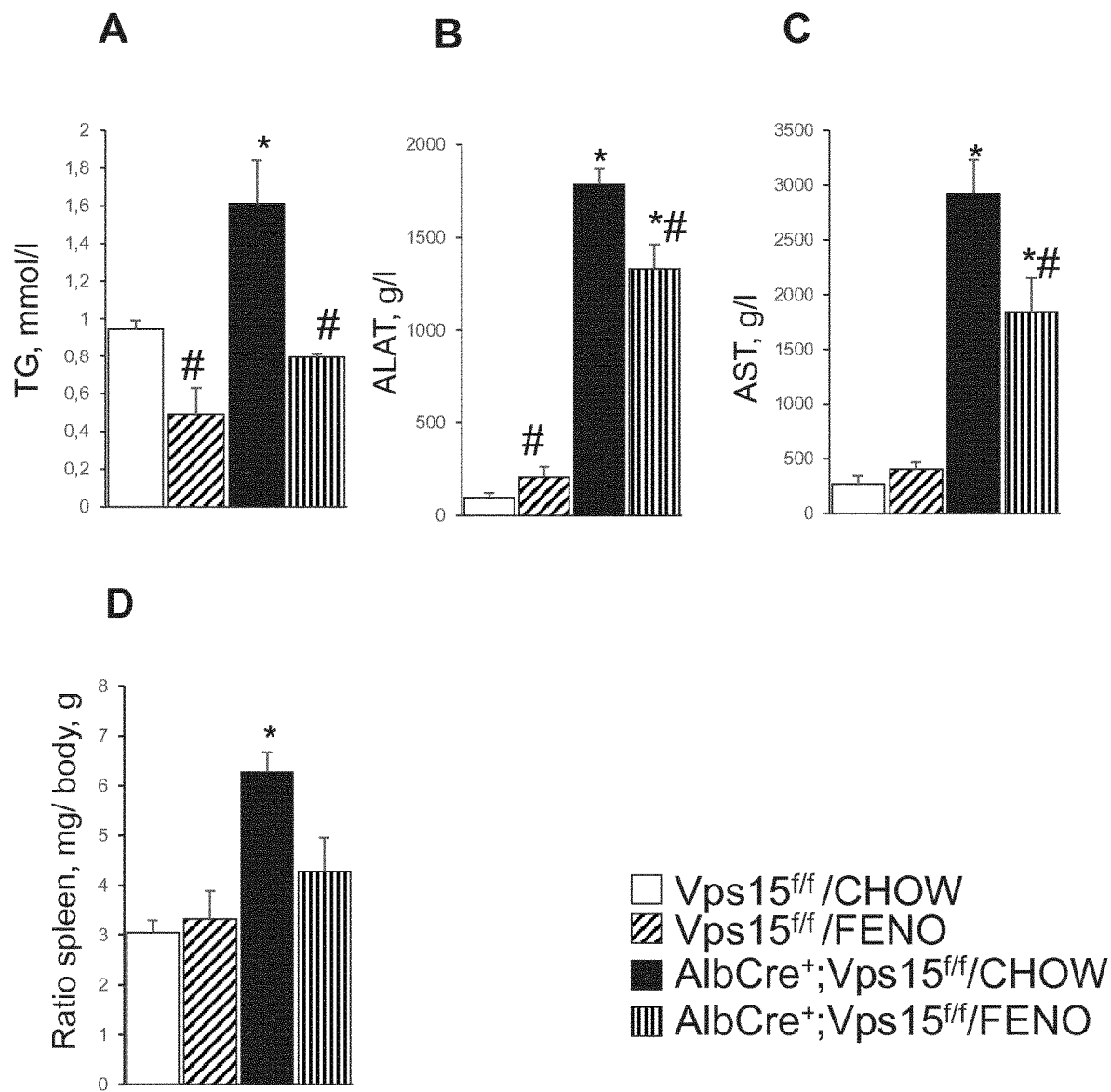

FIG. 8 represents the biochemical analyses of triglyceride levels (FIG. 8A) and activity of alanine transaminase (ALAT) (FIG. 8B) and aspartate transaminase (AST) (FIG. 8C) in plasma of random-fed control and Vps15 LKO mice that were treated for two weeks with fenofibrate incorporated in food or control chow food. FIG. 8D. The spleen hypertrophy as a measure of response to liver damage and chronic inflammation is presented as a ratio of spleen weight to body weight. Data are means±SEM (n=4 for $Vps15^{f/f}$ chow and FENO group, n=3 for AlbCre+; $Vps15^{f/f}$ chow and n=4 for AlbCre+; $Vps15^{f/f}$ FENO group, $P<0.05$*: vs $Vps15^{f/f}$, #: vs chow, 2-tailed, unpaired Student's t test). These analyses show that short-term fenofibrate treatment has a beneficial effect in lowering plasmatic triglycerides and significantly ameliorates liver damage in Vps15 LKO mice.

Figure 9:
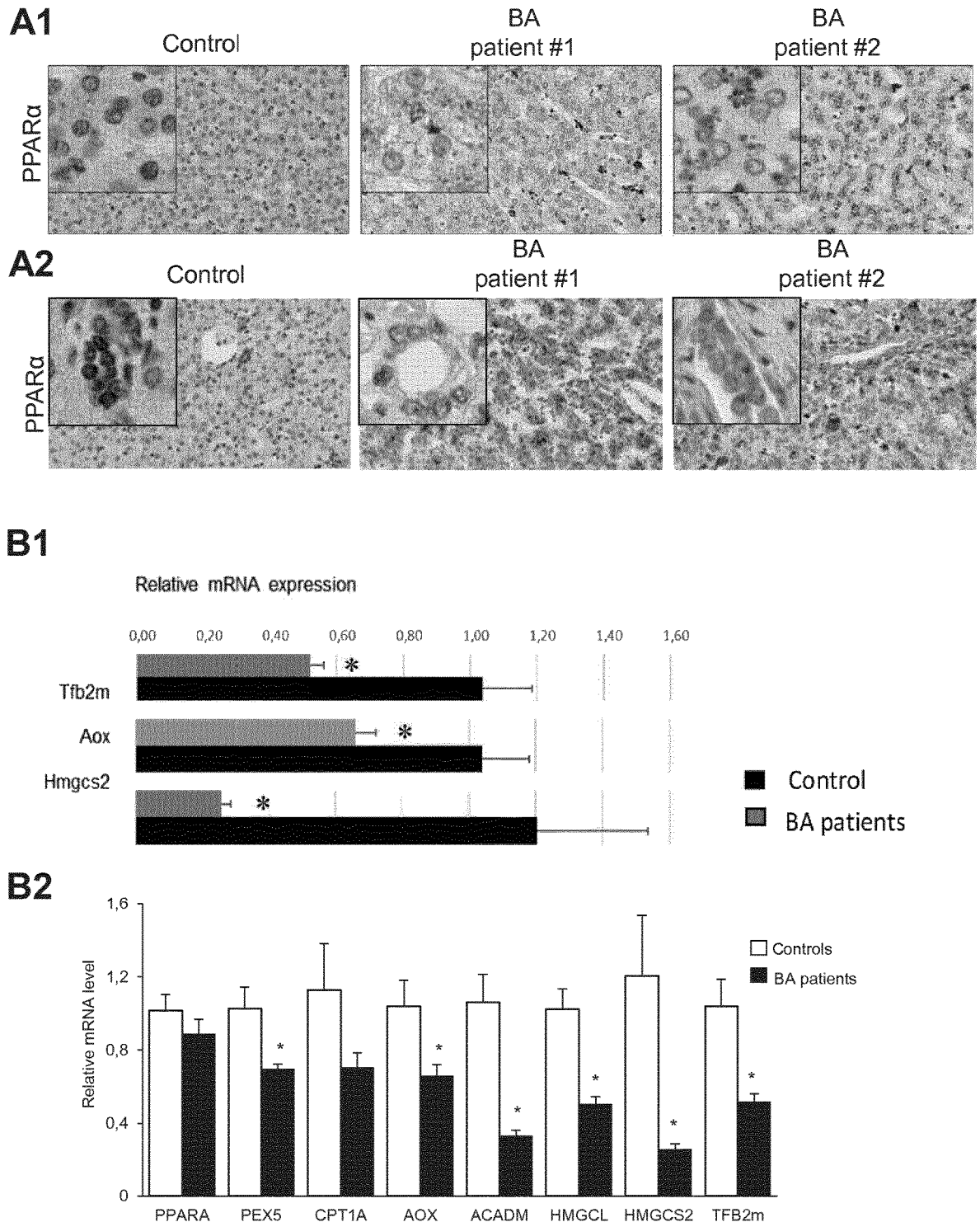

FIG. 9 represents the immunohistological analyses to evaluate PPARα protein expression (FIGS. 9A1 and 9A2) and its target transcript levels (FIGS. 9B1 and 9B2) in liver tissue of BA patients. These analyses show that PPARα expression is nuclear in liver tissue of non-affected by BA individual while it is weakly nuclear and present as granular cytosolic staining both in hepatocytes (FIG. 9A1) and in cholangiocytes (FIG. 9A2) in liver tissue samples of BA patients. The transcript analyses by QRT-PCR (FIGS. 9B1 and 9B2) show that levels of PPARα targets (Tfb2m, Aox, Hmgcs2 (FIG. 9B1) and Pex5, CPT1A, ACADM, HMGCL (FIG. 9B2)) in liver tissue of BA patients are significantly decreased compared to controls while the transcript level of PPARα is unchanged (FIG. 9B2). To conclude, these analyses show that PPARα activity is downregulated in liver of BA patients.

Figures 10A, 10B:
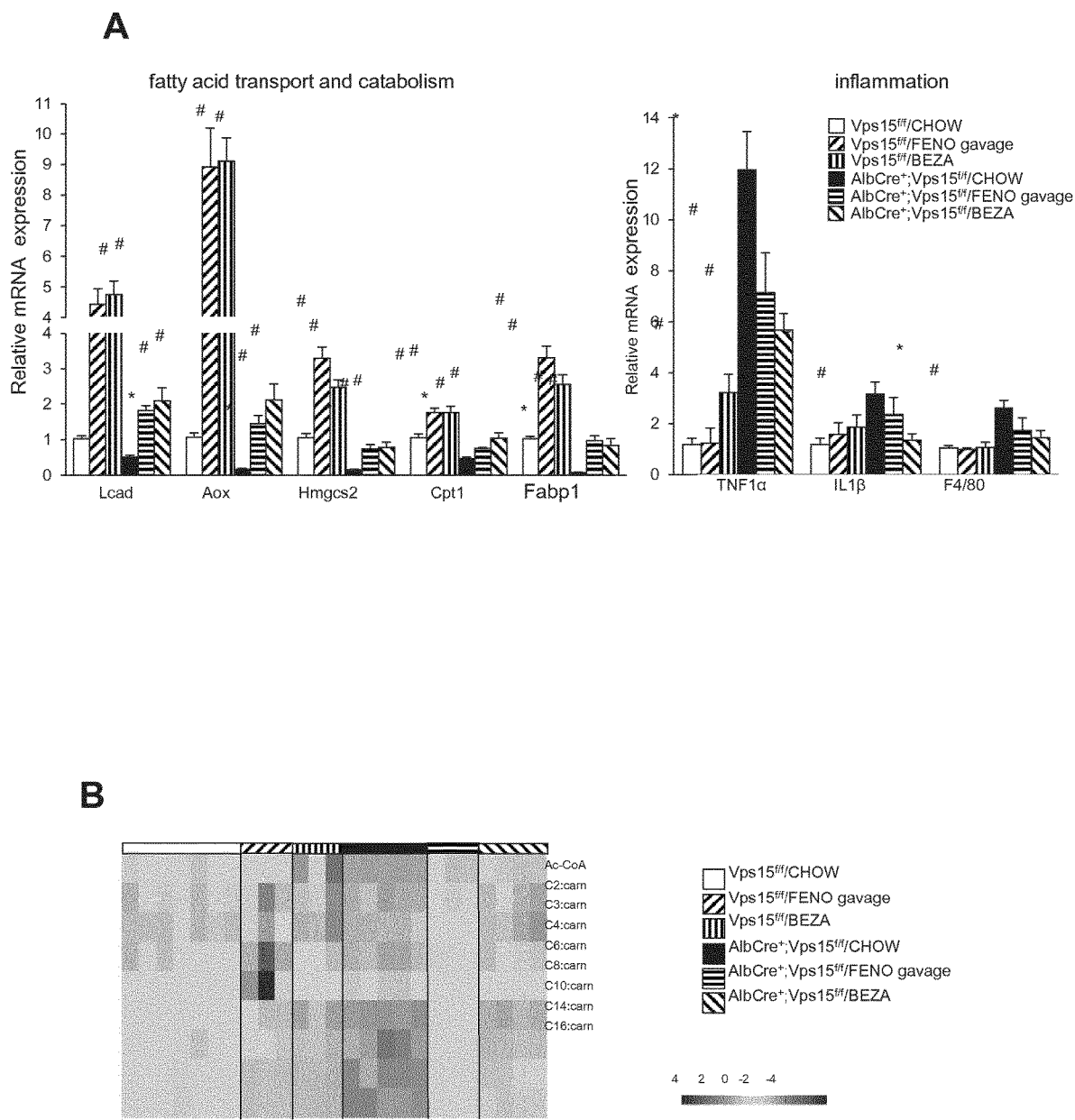
Figure 10C:
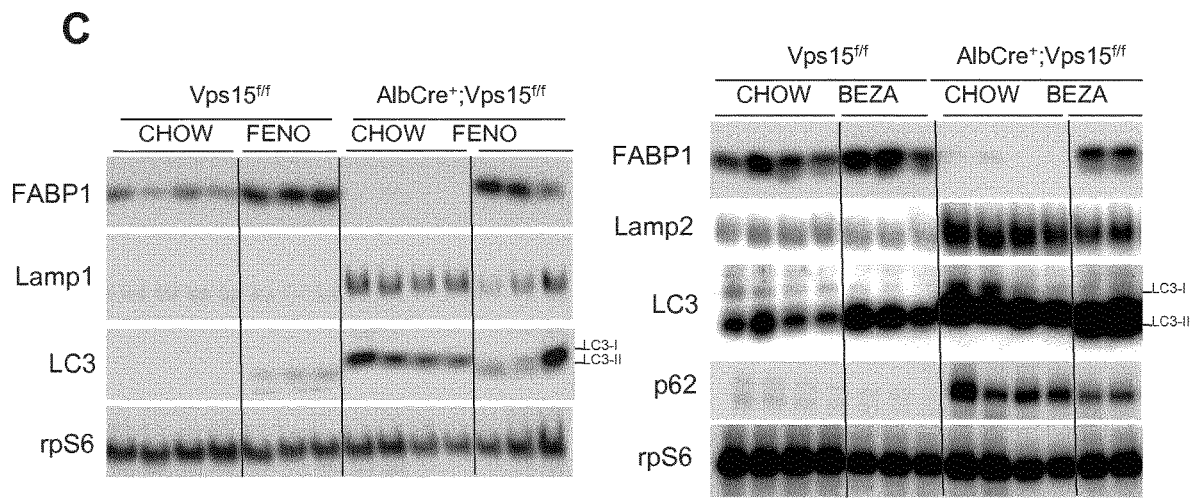

FIG. 10 represents the molecular and metabolic analyses in liver tissue of Vps15LKO mice treated for two weeks with fenofibrate administered once per day with gastric tube (gavage) or bezafibrate incorporated in food (BEZA). FIG. 10A. Transcript level analyses in liver tissue samples showing the restoration of PPARα function by FENO gavage and BEZA in food treatment in Vps15LKO mice. Relative transcript levels of metabolic enzymes in fatty acid transport and catabolism (HMGCS2, CPT1, LCAD, AOX, Fabp1) and inflammation (TNF1α, IL1β, F4/80) in livers of fed control and Vps15LKO mice that were treated for two weeks with fenofibrate or bezafibrate. Data are means±SEM ($Vps15^{f/f}$: n=9 for chow, n=3 for FENO gavage, n=3 for BEZA food; AlbCre+; $Vps15^{f/f}$: n=5 for chow, n=3 for FENO gavage, n=2-4 for BEZA food; $P<0.05$*: vs $Vps15^{f/f}$, #: vs chow, 2-tailed, unpaired Student's t test). FIG. 10B. Heat map representation of metabolomic analyses of acyl-carnitine fatty acid species by mass spectrometry of liver tissue samples of mice treated as in FIG. 10A. Each column represents a biological replicate of liver sample obtained from different mouse. The metabolomic analyses show marked restoration of fatty acid oxidation in livers of Vps15 LKO mice treated with fenofibrate and bezafibrate as judged by decreased levels of long-chain fatty acid carnitines and increased levels of short-chain fatty acid carnitines. FIG. 10C represents immunoblot analyses of total protein liver extracts of mice treated as in FIG. 10A with indicated antibodies. Immunoblot with anti-rpS6 and anti-FABP1 antibodies served as a loading control and control of PPARα target, respectively. Immunoblot with anti-Lamp1 antibody shows that its accumulation in livers of Vps15 mutants is reduced by fenofibrate gavage and bezafibrate in food treatment. In the same way, pharmacologic treatments promoted LC3-lipidation (appearance of LC3-II form) and reduction of p62 accumulation in livers of Vps15LKO mice.

Figure 11:
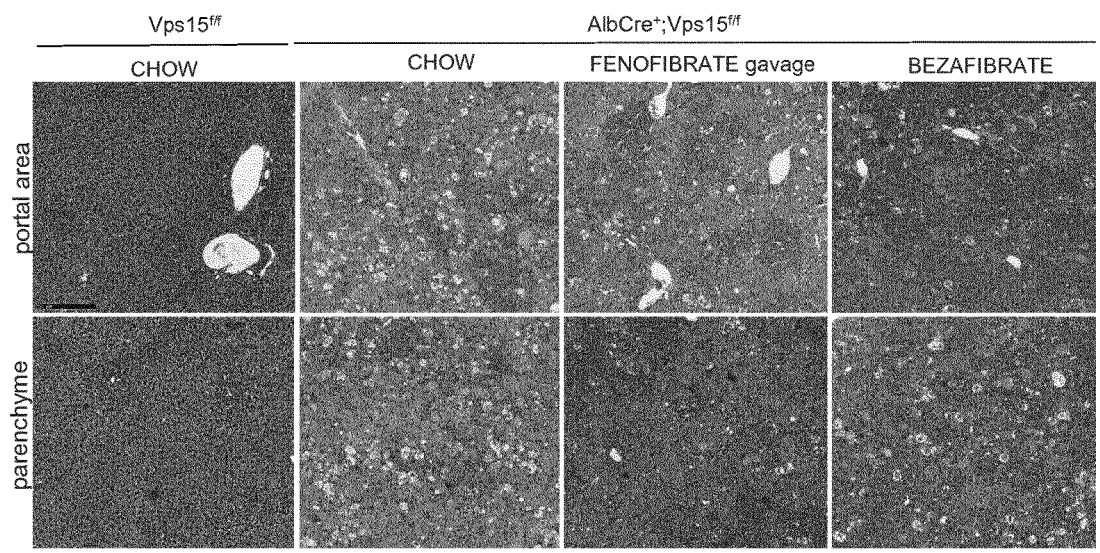

FIG. 11 represents the histological analyses of liver tissue in control and Vps15LKO mice that were treated for short-term with FENO administered by oral gavage and BEZA incorporated in food. Representative images of hematoxylin/eosin staining of formol fixed paraffin embedded liver tissue of control FENO and BEZA treated mice are presented for lobular area (top panel) and portal area (bottom panel). Those captures show that pharmacological activation of PPARα by FENO or BEZA rescues hepatocyte vacuolation and ameliorates architecture of intrahepatic biliary system in livers of Vps15LKO mice. The Examples and Figures illustrate the invention without limiting its scope.

Figure 12:
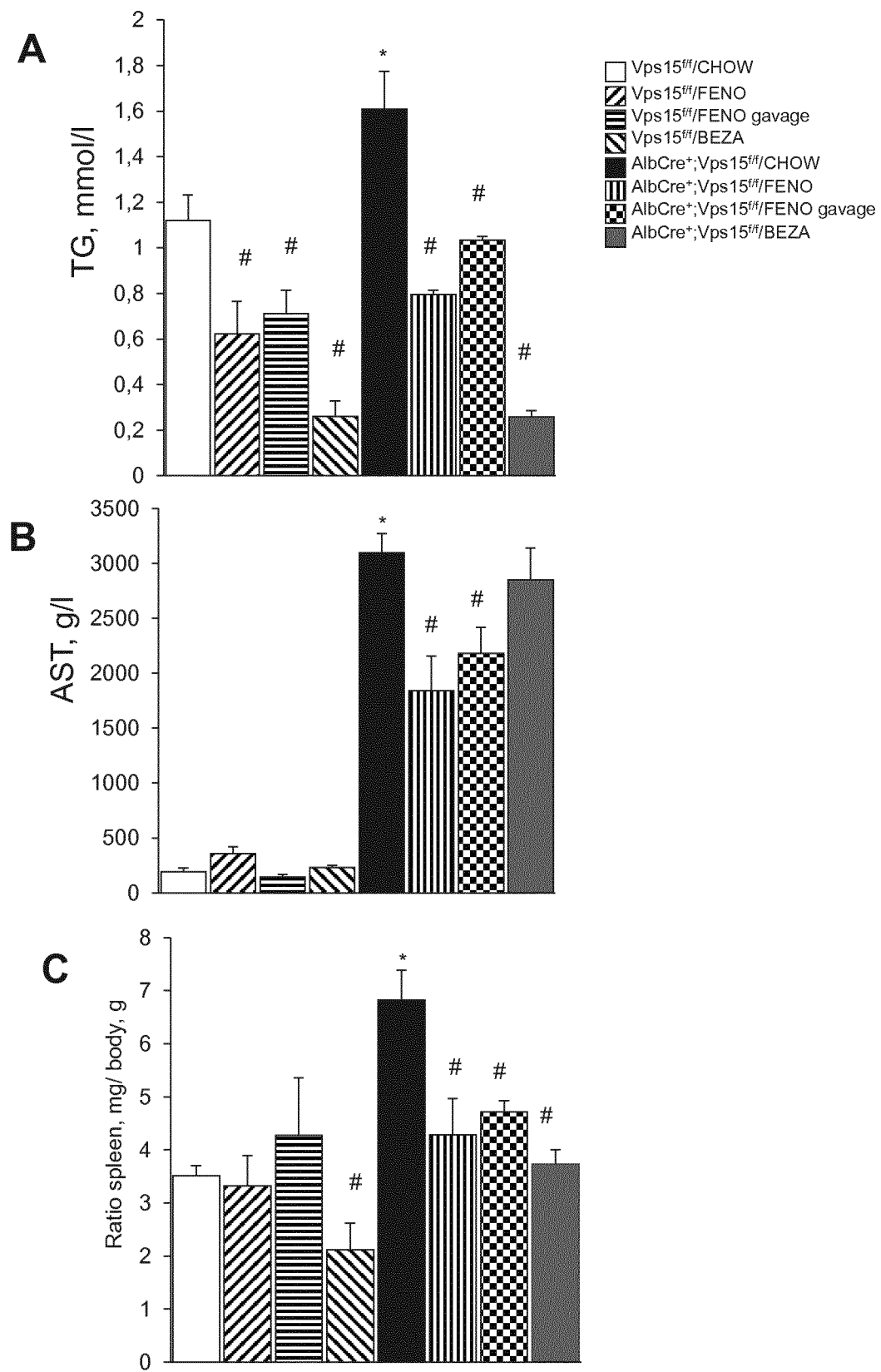

FIG. 12 represents the analyses of plasmatic TG, liver enzyme AST and spleen hypertrophy were extended to the Vps15 LKO mice treated for two weeks with fenofibrate administered once per day with gastric tube (gavage) or bezafibrate incorporated in food (BEZA) similar to conditions as treatment with fenofibrate presented in FIG. 8. Data are means±SEM ($Vps15^{f/f}$: n=10 for chow, n=4 for FENO food, n=3 for FENO gavage, n=3 for BEZA food; AlbCre+; $Vps15^{f/f}$: n=6 for chow, n=4 for FENO food, n=3 for FENO gavage, n=2-4 for BEZA food; P<0.05*: vs Vps15$^{f/f}$, #: vs chow, 2-tailed, unpaired Student's t test). Results show that similar to short-term fenofibrate treatment administered in food, oral administration of fenofibrate once per day or administration of BEZA in food has similar effect in lowering plasmatic triglycerides and decreasing spleen hypertrophy. The administration of fenofibrate once per day was similarly effective judged from three parameters tested (FIG. 12 A, B, C) to the effect of fenofibrate treatment administered in food.

DETAILED DESCRIPTION OF THE INVENTION

As intended herein, the term "comprising" has the meaning of "including" or "containing", which means that when an object "comprises" one or several elements, other elements than those mentioned may also be included in the object. In contrast, when an object is said to "consist of" one or several elements, the object cannot include other elements than those mentioned.

Definitions

The terms "subject", "individual", and "patient" are used interchangeably herein and refer to a mammal being assessed for treatment and/or being treated, more precisely a mammal suffering from biliary atresia or disease associated with biliary system destruction. Subjects are preferably humans, more preferably children, and more preferably neonates, newborns or infants but also include other mammals. The terms "neonates" refers to a newborn baby, specifically a baby in the first 4 weeks after birth, more exactly from the birth to 28 days inclusive. The term "infants" refers to a baby under the age of 1 year, more exactly from the 1th month to 1 year. The term "children" or "child" refers to young human under the age of puberty.

The term "treatment" or "treating" refers to an action, application or therapy, wherein a subject, including a human being, is subjected to medical aid with the purpose of improving the subject's condition, directly or indirectly. Particularly, the term refers to improving symptoms, preventing recurrence, improving prognosis, slowing the progression or combination thereof in some embodiments. The treatment may be curative or at least result in alleviation of symptoms.

The term "Kasai operation" refers to a hepatoportoenterostomy (or its variants) consisting in a resection of obstructed extrahepatic bile duct at the porta hepatitis and anastomosis with small bowel or anastomosis with a part of residual gall bladder or biliary cyst.

The term "fenofibrate" refers to 2-{4-[(4-chlorophenyl)carbonyl]phenoxy}-2-méthylpropanoate de propan-2-yle (CAS no. 49562-28-9) of formula (I) below:

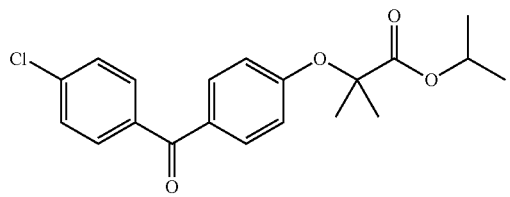 [SMILES: CC(C)OC(=O)C(C)(C)Oc1ccc(C(=O)c2ccc(Cl)cc2)cc1]

The term "ciprofibrate" refers to (RS)-2-[4-(2,2-dichlorocyclopropyl)phenoxy]-2-mëthylpropanoïque (CAS no. 52214-84-3) of formula (II) below:

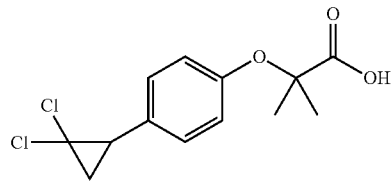 [SMILES: CC(C)(Oc1ccc(C2CC2(Cl)Cl)cc1)C(=O)O]

The term "gemfibrozil" refers to 5-(2,5-diméthylphénoxy)-2,2-diméthyl-pentanoïque (CAS no. 25812-30-0) of formula (III) below:

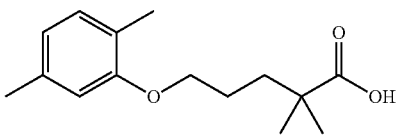 [SMILES: Cc1ccc(C)c(OCCCC(C)(C)C(=O)O)c1]

The term "bezafibrate" or "BZ" refers to 2-(4-(2-((4-chlorobenzoyl)amino)ethyl)phenoxy)-2-methylpropanoic acid (CAS no. 41859-67-0) of formula (IV) below:

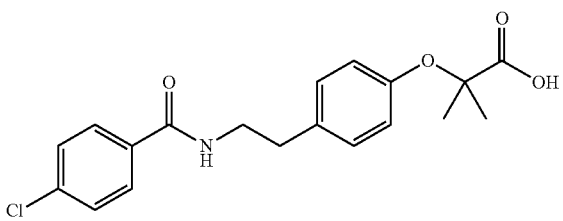 [SMILES: CC(C)(Oc1ccc(CCNC(=O)c2ccc(Cl)cc2)cc1)C(=O)O]

The term "Clinofibrate" or "Lipoclin" refers to 2-[4-[1-[4-(2-carboxybutan-2-yloxy)phenyl]cyclohexyl]phenoxy]-2-methylbutanoic acid (CAS no. 30299-08-2) of formula (V) below:

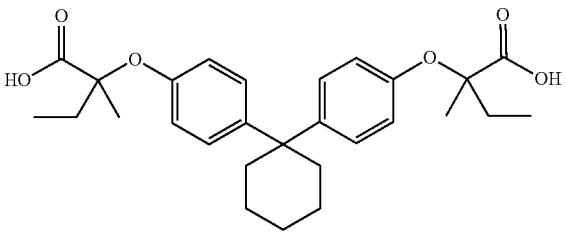 [SMILES: CCC(C)(Oc1ccc(C2(c3ccc(OC(C)(CC)C(=O)O)cc3)CCCCC2)cc1)C(=O)O]

The term "Clofibrate" refers to ethyl 2-(4-chlorophenoxy)-2-methylpropanoate (CAS no. 637-07-0) of formula (VI) below:

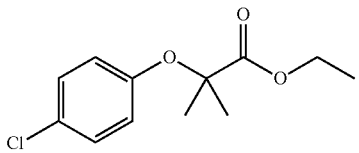 [SMILES: CCOC(=O)C(C)(C)Oc1ccc(Cl)cc1]

The term "Clofibride" refers to 3-(dimethylcarbamoyl) propyl 2-(4-chlorophenoxy)-2-methylpropanoate (CAS no. 26717-47-5) of formula (VII) below:

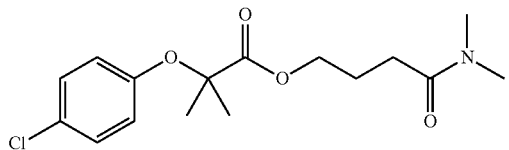 [SMILES: CN(C)C(=O)CCCOC(=O)C(C)(C)Oc1ccc(Cl)cc1]

The term "Ronifibrate" refers to 3-{[2-(4-chlorophenoxy)-2-methylpropanoyl]oxy}propyl nicotinate (CAS no. 42597-57-9) of formula (VIII) below:

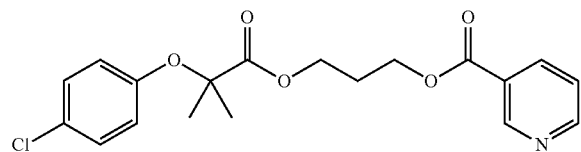 [SMILES: CC(C)(Oc1ccc(Cl)cc1)C(=O)OCCCOC(=O)c1cccnc1]

The term "Simfibrate" refers to propane-1,3-diyl bis[2-(4-chlorophenoxy)-2-methylpropanoate] (CAS no. 14929-11-4) of formula (IX) below:

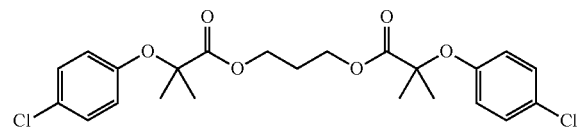 [SMILES: CC(C)(Oc1ccc(Cl)cc1)C(=O)OCCCOC(=O)C(C)(C)Oc1ccc(Cl)cc1]

The term "Elafibranor" refers to 2-[2,6-dimethyl-4-[(1E)-3-[4-(methylthio)phenyl]-3-oxo-1-propen-1-yl]phenoxy]-2-methyl-propanoic acid (CAS no. 923978-27-2).

Therapeutic Uses

Despite the knowledge of the prior art, according to which fibrates compounds target metabolic disorders, mainly hypercholesterolemia, and are therefore hypolipidemic agents, the inventors surprisingly found that fibrate compounds could be useful in treating a patient suffering from biliary atresia. Thus, making it possible to obtain an improvement of liver functionality.

The term "liver functionality" refers to many functions of the liver in the body, including making proteins and blood clotting factors, manufacturing triglycerides and cholesterol, glucose and ketone bodies production, glycogen synthesis, and bile production. The term "improvement of liver functionality" includes the preservation of hepatocytes and biliary ducts including intrahepatic and extrahepatic ducts and so, the preservation of a functional bile flow. The liver is considered functional when it is capable of performing at least one of its physiological functions. In particular, the liver function is considered as maintained if level of at least one physiological parameter indicative of liver function is essentially constant between two or more time points, i.e. the difference between the two time points does not exceed a medically acceptable tolerance.

According to the invention, the inventors showed that fibrate compound, preferably fenofibrate or bezafibrate, activated autophagy and improved liver functionality. Inventors showed that the invention contributes to improved liver structure and intra-hepatic biliary system. In particular, the inventors showed that the model of Vps15 LKO mice reunites major intrahepatic manifestations of BA disease and, therefore, could be used for pharmacological studies in BA. The inventors showed that autophagy is inhibited and expression of the class 3 PI3K subunits is decreased in a large proportion of BA patients. The inventors demonstrated that nuclear PPARα expression and activity is decreased in liver tissue of BA patients.

Altogether, these findings confirm that fibrate compounds are good candidates to have therapeutically beneficial effects on the structure and the function of the liver and the biliary system of BA patients. Finally, fibrate compounds are good candidates for treating biliary atresia.

In a first aspect, the present invention relates to fibrate compounds for its use in the treatment of biliary atresia or disease associated with biliary system destruction.

In particular, the present invention relates to fibrate compounds which are specifically an agonist of the alpha form of PPAR, more preferably an agonist of the alpha form of PPAR except the elafibranor. In a more preferred embodiment, fibrates compounds are fenofibrate and/or bezafibrate.

Unexpectedly, the inventors found that transcription factor of nuclear receptor superfamily PPARα is inhibited in the mouse model of Vps15LKO. Also, the inventors showed after metabolomics and transcriptomic analyses of liver tissue of Vps15LKO mice, a defective metabolism including inhibition of ketogenesis and fatty acid beta oxidation. The inventors have highlighted low levels of hydroxybutyrate representing a defective ketogenesis and accumulation of long-chain fatty acid carnitine derivatives representing an inhibition of fatty acid β-oxidation. Importantly, the transcript levels of the key enzymes of these metabolic pathways were downregulated showing the defects at transcriptional level. Also, these two pathways are positively controlled by PPARα transcription factor. The inventors also show that similar to fenofibrate, the treatment with bezafibrate agonist of PPARα had improved PPARα activity in livers of Vps15LKO mice. These observations demonstrate the positive effect of PPARα agonist beyond fenofibrate. Furthermore, the inventors show that administration to Vps15 LKO mice of fenofibrate in the regiment one dose per day by oral gavage has similar effect on PPARα activation and metabolic amelioration of fatty acid oxidation to the treatment with fenofibrate administered with food. Thus, it is preferred to use a fibrate compound which is specific to the alpha form of PPAR to obtain a significant biological effect.

Fibrates are a class of amphipathic carboxylic acids and are used for a range of metabolic disorders, mainly hypercholesterolemia, and are, therefore, hypolipidemic agents. Fibrates activate PPAR, especially PPARα. The PPARs are a class of intracellular receptors that modulate carbohydrate, lipid metabolism and adipose tissue differentiation. Activating PPARs induces the transcription of a number of genes that facilitate lipid metabolism. They are used in many hyperlipidemias. Fibrates are used in accessory therapy in many forms of hypercholesterolemia, usually in combination with statins. Fibrates reduce the number of non-fatal heart attacks, but do not improve all-cause mortality and are therefore indicated only in those not tolerant to statins.

In a preferred embodiment, the fibrate compound is chosen from the group consisting in fenofibrate, ciprofibrate, gemfibrozil, bezafibrate, clinofibrate, clofibrate, clofibride, ronifibrate and simfibrate, more preferably, fenofibrate and/or bezafibrate.

In another embodiment, the invention relates to a combination of fenofibrate and bezafibrate for its use in the treatment of biliary atresia.

In another embodiment, fibrate compound is administered to a neonate, an infant or a child. As discussed above, the causes of BA remain actually unknown. BA is a neonatal disease. There are no cases reported in adults, certainly because the principal bile duct is totally obstructed. Thus, it is 100% lethal if no surgical operation is performed such as Kasai intervention or liver transplantation. At the end, very few patients are alive with their native liver to the adulthood (10 to 15% max of patients after 20 years of age and probably less than 10% after 30 years of age). Because of the good results of the liver transplantation, most of the patients are alive after liver transplantation at adulthood.

In another embodiment, fibrate compound is administered to a subject once a day, preferably once during the next 12 hours. In particular, fibrate compound is administered to a subject in line with the physiological cycle of PPARα transcriptional activity, preferably before night fast.

The invention also provides a pharmaceutical composition comprising fibrate compound, preferably fenofibrate and/or bezafibrate for its use in the treatment of biliary atresia.

According to the invention, the pharmaceutical composition may be formulated in the form of injectable suspensions, gels, oils, pills, tablets, suppositories, powders, gel caps, capsules, aerosols or means of galenic forms or devices assuring z prolonged and/or slow release.

A pharmaceutical composition comprising fibrate compound, preferably fenofibrate and/or bezafibrate for its use in the treatment of biliary atresia can be formulated in the form of a "kit-of-parts" for a co-administration in the treatment of biliary atresia.

In another embodiment, the present invention is a method for treating biliary atresia or disease associated with biliary system destruction in a patient in need thereof, comprising administering to said patient a therapeutically efficient amount of a fibrate compounds.

Slowing the Progression and/or Preventing BA

In a second aspect, the present invention relates to fibrate compounds for its use in slowing the progression of BA or disease associated with biliary system destruction. The inventors surprisingly found that fibrate compounds ameliorate the disease and slowed down its progression at the level of intra hepatic bile ducts.

In a preferred embodiment, fibrate compound is administered before and/or after Kasai operation consisting of hepatoportoenterostomy (resection of obstructed extrahepatic bile duct and anastomosis with small intestine). This is relevant for the patient situation as the success of hepatoportoenterostomy surgery depends on the functionality of the intrahepatic biliary system. In the same line, after Kasai operation the treatment could be to restore or prevent the intra hepatic bile duct degeneration, therefore prolonging its beneficial effect on native liver organ function. In turn, it will improve the percentage of success of Kasai operation that could prevent important number of liver transplantation. Finally, the treatment of the present invention can slow or revert the hepatocyte degeneration. Thus, the treatment could have the effect both on hepatocyte and biliary ducts damaged in liver of BA patient. In a preferred embodiment, the treatment is privileged to BA patients post Kasai operation to improve the intrahepatic biliary system function and ameliorate hepatocyte parenchyma postponing the need of liver transplantation. Alternately, the treatment can be administered to BA patient before Kasai operation to improve the intrahepatic biliary system function and ameliorate hepatocyte parenchyma postponing the need of liver transplantation.

Thus, the present invention relates to fibrate compounds for its use in preventing the progression of BA or disease associated with biliary system destruction.

In another embodiment, the present invention is a method for slowing the progression biliary atresia or disease associated with biliary system destruction or for preventing biliary atresia or disease associated with biliary system destruction in a patient in need thereof, comprising administering to said patient a therapeutically efficient amount of a fibrate compounds.

EXAMPLES

Materials and Methods

Reagents

The following primary antibodies were used: Vps15 (1:1000, Abnova, H00030849-M03; 1:1000, Genetex, GTX108953), β-actin (1:5000, Sigma, A5316), Lamin A/C (1:1000, Cell Signaling, 2032), LC3 (1:1000, NanoTools, 0231-100/LC3-3-5-5F10), PPARα (1:500, Santa Cruz, sc-398394, sc-9000), GAPDH (1:1000, Santa Cruz, S.C.-25778), Beclin-1 (1:1000, Cell Signaling, 3495), UVRAG (1:1000, Cell Signaling, 13115S), LAMP1 (1:1000, Abcam, ab24170), LAMP1 (1:1000, Abcam, ab25245), LAMP2 (1:1000, Abcam, ab13524), PI3 Kinase Class III Vps34 (1:1000, Cell Signalling, 4263), Ambra1 (1:1000, Cell Signaling, 24907), rpS6 (1:1000, Cell Signalling, 2317), FABP1 (1:1000, Santa Cruz, sc-374537), cytokeratin (1:500, AbCyst, 7VMA3226), SQSTM1 (1:1000, Abnova, H00008878-M01), Atg14 (1:1000, Cell Signaling, 96752), BrdU (1:500, Roche, BMC931), F4/80 (1:500, AbD Serotec, MCA497R).

Animals

The Vsp15 conditional mutant mouse line was established at the MCI/ICS (Mouse Clinical Institute—Institute Clinique de la Souris, Illkirch, France) as described (Nemazanyy, I. et al. Defects of Vps15 in skeletal muscles lead to autophagic vacuolar myopathy and lysosomal disease. EMBO Mol. Med. (2013). Liver specific Vps15 knockout mouse line was generated as described (Nemazanyy I et al., Class III PI3K regulates organismal glucose homeostasis by providing negative feedback on hepatic insulin signalling. Nat Commun. 2015 Sep. 21; 6:8283.). Mice were housed in specific pathogen-free conditions. Male mice (5-8-week-old) were used for the experimentation. Mice were randomly allocated to experimental groups and at least three animals were used for each condition (as indicated in figure legends) to ensure statistics analyses. Animal numbers were chosen to reflect the expected magnitude of response that takes into account the variability observed in previous experiments. All animal studies were approved by the Direction Départementale des Services Vétérinaires, Prefecture de Police, Paris, France (authorization number 75-1313) and the ethical committee of Paris Descartes University (17-052).

Treatments and Metabolic Studies In Vivo

All animals used in the study were fed ad libitum standard chow diet (Teklad global protein diet; 20% protein, 75% carbohydrate, 5% fat) and kept under 12 h/12 h (8 am/8 pm) light on/off cycle. Animals were sacrificed between 2-4 pm unless indicated. Fenofibrate (200 mg/kg) or Bezafibrate (0.5%) was incorporated in chow food or given as a single dose by gavage treatment (at ZT1) and mice treated during two weeks with free access to control and drug incorporated food. For 5-bromo-2'deoxyuridine (BrdU) incorporation, mice were treated with BrdU (3 mg/ml, Sigma-Aldrich) dissolved in drinking water for 3 days before sacrifice.

Animals were sacrificed between 2-4 pm unless indicated. For immunohistochemical analysis liver tissue was fixed overnight in phosphate-buffered 10% formalin and embedded in paraffin. 6 µM sections were cut and processed either for staining with eosin/hematoxylin, Sirius Red or for immunohistochemical analyses. Plasmatic TG, Billirubin, Hydroxybutyrate, AST and ALAT activities were measured enzymatically using Olympus AU 400 apparatus.

Histological and Morphometric Analyses

For immunohistochemical analysis, liver tissue was fixed overnight in phosphate-buffered 10% formalin and embedded in paraffin. 4 µm sections were cut and processed either for staining with eosin/hematoxylin or for immunohistochemical analyses. Post-staining analyses were performed on digitalized with the NanoZoomer S210 (Hamamatsu) liver tissue slices. Immunohistochemistry of liver tissue sections was performed using anti-p62 (Abnova), anti-TROMA-III-s (DSHB), anti-cytokeratin (AbCyst) or with anti-Lamp1 (Abcam) antibodies.

Subcellular Fractionation

Nuclear fractions were prepared from 50 mg of liver tissue using NE-PER Kit (Pierce) according to manufacturer's recommendations.

Protein Extraction and Immunoblotting

To prepare protein extract for immunoblot analysis, liver tissue was homogenized in lysis buffer containing 20 mM Tris-HCl (pH 8.0), 5% glycerol, 138 mM NaCl, 2.7 mM KCl, 1% NP-40, 20 mM NaF, 5 mM EDTA, 1× protease inhibitors (Roche), 1× PhosphoStop Inhibitors (Roche). Homogenates were spun at 12000×g for 10 min at 4° C. Protein extracts were resolved by SDS-PAGE before transfer onto PVDF membrane followed by incubation with the primary antibodies and HRP-linked secondary antibodies. Immobilon Western Chemiluminescent HRP Substrate (Millipore) was used for the detection. The images were acquired using ChemiDocTouch Imaging System (BioRad) and the quantification performed using ImageJ software.

Targeted Metabolomics

Targeted metabolomics analyses were performed on liver tissue extracts obtained with solution of 50% methanol, 30% ACN, and 20% water. The volume of extraction solution added was calculated from weight of powdered tissue (60 mg/ml). After addition of extraction solution, samples were vortexed for 5 min at 4° C., and then centrifuged at 16,000×g for 15 min at 4° C. The supernatants were collected and analysed by liquid chromatography-mass spectrometry using SeQuant ZIC-pHilic column (Merck) for the liquid chromatography separation. Mobile phase A consisted of 20 mM ammonium carbonate plus 0.1% ammonia hydroxide in water. Mobile phase B consisted of ACN. The flow rate was kept at 100 ml/min, and the gradient was 0 min, 80% of B; 30 min, 20% of B; 31 min, 80% of B; and 45 min, 80% of B. The mass spectrometer (QExactive Orbitrap, Thermo Fisher Scientific) was operated in a polarity switching mode and metabolites were identified using TraceFinder Software (Thermo Fisher Scientific). For analyses, metabolomics data were normalized using the median normalization method. MetaboAnalyst 4.0 software was used for heatmaps generation. The algorithm for heatmap clustering was based on the Pearson distance measure for similarity and the Ward linkage method for biotype clustering.

Real-Time Quantitative PCR

Total RNA was isolated from liver tissue using RNAeasy Lipid Tissue Mini Kit (Qiagen). Single-strand complementary DNA was synthesized from 1 µg of total RNA using 125 ng of random hexamer primers and SuperScript II (Life Technologies). RT-qPCR was performed on MX3005P instrument (Agilent) using a Brilliant III Ultra-Fast QPCR Master Mix (Agilent). The relative amounts of the mRNAs studied were determined by means of the $2^{-\Delta\Delta C_T}$ method, with pinin, S18, cyclophilin, eIF2α, HUS, Ubiquitin as reference genes for studies in mice and pinin for studies in human patient samples.

Statistical Analysis

Data are shown as means±SEM. The unpaired two-tailed Student's t-test was applied for statistical analysis. Results were considered significant in all experiments at $P<0.05$.

Results

Autophagic Degradation is Blocked in Liver Tissue of BA Patients

The obliteration of the entire extrahepatic and intrahepatic biliary system is a major pathognomonic manifestation of the BA. Importantly, histologic findings in liver explants of BA patients also strongly advocate that, with the disease progression, in the liver, the hepatocytes are equally affected and show marked ballooning, vacuolation and accumulation of the deposits such as bile, copper, copper-binding proteins and Mallory-Denk bodies. Those degenerative findings in both cholangiocytes and hepatocytes made the inventors to hypothesize that defects in a fundamental homeostatic process present in all cells might drive BA. Autophagy is one of such essential homeostatic metabolic pathways that functions in all eukaryotic cells to assure cellular fitness. To establish if the autophagic degradation is intact in the livers of BA patients, the immunohistological analyses of an autophagy cargo receptor, p62/SQSTM1, and an integral lysosomal membrane protein Lamp1 protein were performed. The accumulation of both proteins was observed in liver samples of BA patients (arrow) compared to non-BA controls (FIG. 1). As control, the liver tissue samples of patients with hepatocellular adenoma (a non-tumoral part of the liver biopsy), patients with oxalosis, methylmalonic acidemia (MMA), ornithine transcarbamylase deficiency (OTC), and two samples of liver tissue from healthy donor for liver transplantation were used. Notably, 12 out of 14 BA patient samples were positive for p62 staining while accumulation of Lamp1 protein was observed in 8 out of 8 patient liver samples. Importantly, the positive staining was uniformly distributed in liver tissue samples with both hepatocytes and cholangiocytes showing p62 and Lamp1 accumulation. Thus, the combination of these histological analyses shows that autophagic degradation is blocked in liver tissue of BA patients.

Inactivation of the Class 3 PI3K in Mouse Liver Phenocopies Hepatic Manifestations in BA Patients Given the observations of defective autophagic degradation in liver tissue of BA patients, the inventors asked whether the mouse model of defective autophagy and lysosomal trafficking by inactivation of the class 3 PI3K in both hepatocytes and cholangiocytes would mimic the hepatic manifestations of BA. For that, the analyses of liver-specific Vps15-deficient AlbCre+; Vps15$^{f/f}$ mice, hereafter referred to as Vps15 LKO, were performed. The Vps15 LKO mice manifested severe liver hypertrophy (Nemazanyy I et al., Class III PI3K regulates organismal glucose homeostasis by providing negative feedback on hepatic insulin signalling. Nat Commun. 2015 Sep. 21; 6:8283.). Furthermore, in agreement with the requirement of class 3 PI3K for autophagy, the deletion of Vps15 resulted in autophagy block, as witnessed by accumulation of p62 and Lamp1 (arrow) proteins revealed by immunohistological analyses (FIG. 2A). In addition, Vps15-deletion provoked striking vacuolization consistent with defective endocytic trafficking. These were accompanied by the prominent hepatocyte damage reflected by significantly increased activity of transaminases and bilirubin levels in plasma of Vps15 LKO mice that was evidently grey colored (FIG. 2B). The liver damage provoked significant inflammation and proliferation of both hepatocytes and cholangiocytes (strong ductal reaction) as detected by increased F4/80 staining and marked BrdU incorporation in the livers of Vps15 LKO mice (FIG. 2C). Those were also accompanied by increased apoptosis detected by TUNEL assay (FIG. 2C). Finally, the inactivation of the class3 PI3K in hepatocytes and cholangiocytes led to pathological fibrotic liver degeneration revealed by Sirius Red and Trichrome staining (FIG. 2D). Altogether, histological analyses show that Vps15 deletion in intrahepatic biliary system and in hepatocytes provokes manifestations reminiscent of the ones observed in liver of BA patients.

The Vps15 Deletion Results in Deleterious Intrahepatic Biliary Degeneration Reminiscent of BA To get further insights into whether hepatic Vps15 depletion mimics the alterations seen in BA, the comparative histological analyses of BA liver tissue biopsies of patients and livers of Vps15 LKO mice were performed. First, the sections of HE stained BA patient liver samples collected at the time of the liver transplantation for the children who have failed Kasai operation (BA patient #1) and liver samples collected at the time of Kasai operation (BA patient #2) were compared to sections of liver tissue of Vps15 LKO mice. As seen on FIG. 3A, both types of tissue samples are characterized by marked portal triad degeneration with obliterated portal bile ducts, intrahepatic cholestasis, giant hepatocytes, portal fibrosis, intrahepatic bile duct proliferation in the portal tracks and severe infiltration with the inflammatory cells (arrow). Further immunohistological analyses with anti-cytokeratin (anti-CK19) antibodies to label the hepatic biliary ducts, have highlighted the similarities between the BA patient liver and Vps15 LKO mouse liver samples. The biliary ducts in the portal area were disorganized in livers of Vps15 LKO mice (FIG. 3B. The most importantly, the deletion of Vps15 hepatic progenitors provoked massive ductal reaction both in the portal area and in the hepatic parenchyma (FIG. 3B). Thus, these observations show that Vps15 LKO mouse model presents an array of the hepatic and biliary phenotypes that are highly reminiscent of BA manifestations in human patients showing that defective autophagy might underline the biliary duct obliteration and liver failure in BA.

The Expression of the Class 3 PI3K Subunits is Defective in Liver Tissue of BA Patients To get further molecular insights in the defects of autophagic pathway in liver tissue of BA patients, the protein expression of the class 3 PI3K subunits in total liver protein extracts of a cohort of 30 BA patients was analyzed (FIG. 4A). In these analyses, six samples were used as controls. Those included a healthy liver graft and liver tissue samples from patients with unrelated to BA liver diseases that do not affect liver structure neither hepatocytes nor biliary ducts (oxalosis, ornithine transcarbamylase deficiency and methylmalonic acidemia). The immunoblot analyses were subjected to quantification of the band intensities which were normalized to a total protein amount loaded on each lane and presented for each patient as fold changes compared to the signal obtained in the group of control liver samples. As a result, the expression levels of the class 3 PI3K subunits was heterogenous in liver tissue samples of BA patients (FIG. 4B). Notably, as expected, there was a positive correlation in the expression levels between the catalytic and the regulatory subunits in the class 3 PI3K complex. To this end, a decrease in protein levels of Vps15 was accompanied by a decreased expression of Vps34. These analyses revealed three groups depending on the expression of core subunits of the class 3 PI3K, Vps15 and Vps34 proteins. The groups A, B and C consisted 12, 10 and 8 BA patients, respectively, and represented equal to controls, around 30-40% decreased and below 50% expression (FIGS. 4A and 4B). In the group A, expression of the core and regulatory subunits of the class 3 PI3K with an exception of Ambra1 was not modified. Notably, the patients in group C presented a depletion of all subunits of the class 3 PI3K. In group B, the expression of all class 3 PI3K subunits was significantly but intermediately decreased compared to controls (FIG. 4B). Altogether, these analyses show that expression of the class3 PI3K in one third of BA patients is severely downregulated advocating the class 3 PI3K dysfunction and autophagic inhibition as a putative pathological mechanism in BA disease.

PPARα Transcriptional Activity is Inhibited in Vps15-Null Liver and could be Rescued by Fenofibrate The inventors have discovered that Vps15 LKO mice have also presented the severe metabolic dysfunction such as inability to sustain functional mitochondrial oxidation of fatty acids. Surprisingly, this metabolic dysfunction of Vps15 LKO mice was reminiscent of a deficiency of PPARα, a nuclear receptor that orchestrates in the liver and is essential fatty acid uptake, transport, β-oxidation and ketogenesis. Similarly, to reported mouse mutants of PPARα, Vps15LKO mice were hypoketogenic (FIG. 5A) and hypoglycaemic. In agreement with its transcriptional inhibition, nuclear PPARα protein was depleted in Vps15-null livers (FIG. 5B). PPARα protein expression, stability and nuclear localization are controlled by a direct ligand binding. The available selective synthetic ligands of PPARα, like fenofibrate, are efficient in pharmacotherapy of hyperlipidaemias by promoting fatty acid uptake, transport and oxidation. The inventors hypothesized that pharmacologic treatment with fenofibrate could be efficient in restoring PPARα transcriptional activity and correcting metabolic defects in the Vps15 hepatic mutant. To this end, Vps15 LKO mice were treated during two weeks with fenofibrate incorporated in food. Importantly, fenofibrate induced in control mice a robust increase in transcript expression of key PPARα target genes (FIG. 5C). These include PPARα targets for fatty acid transport (Cpt1), ketogenesis (Hmgcs2) and FAO (Lcad and Aox). Importantly, in Vps15 LKO mice, administration of the synthetic ligand was sufficient to restore PPARα transcriptional activity, at least to levels observed in chow-fed control mice (FIG. 5C). Similarly, the fenofibrate treatment of Vps15 LKO mice was effective in reducing significantly the inflammation (as measured by levels of cytokines TNF1α, IL1β and marker of macrophages F4/80) and intrahepatic fibrosis (as measured by levels of Acta2) (FIG. 5C). The later observation prompted inventors to evaluate further the fibrosis status in livers of Vps15 LKO mice. Notably, the quantification of Sirius Red staining of liver tissue slices of control and treated with fenofibrate Vps15 LKO mice has demonstrated that significantly increased collagen deposition in livers of Vps15 LKO mice was lower in mice treated with fenofibrate incorporated in food (FIG. 5D). Therefore, administration of synthetic ligand fenofibrate restores PPARα transcriptional activity, reduces inflammation and results in decreased fibrosis in liver of Vps15 LKO mice.

Fenofibrate Administration Improved Liver Function of Vps15LKO Mice

In the context of BA, to address whether transcriptional activation of PPARα by fenofibrate had a therapeutic impact on liver function, the inventors performed histological evaluation in liver tissues of control and Vps15 LKO mice treated with fenofibrate. In control mice, fenofibrate administration resulted in hepatocyte hypertrophy (FIG. 6A). At the same time, gross microscopic analyses of liver tissue in Vps15 LKO mice revealed that short-term fenofibrate treatment was sufficient to significantly decrease hepatocyte vacuolation, reduce hepatocyte volume and inflammatory cell infiltration (FIG. 6A). Furthermore, pharmacological activation of PPARα was effective in improving the portal area organization in livers of Vps15 LKO mice witnessed by markedly decreased ductal reaction in liver parenchyma and increased area of portal lumen with present organized biliary ducts (FIG. 6B). Thus, pharmacological activation of PPARα by a synthetic ligand incorporated in food is sufficient to significantly ameliorate liver tissue organization of Vps15 LKO mice which is consistent with decreased inflammation and fibrosis observed in Vps15 hepatic mutants treated with fenofibrate (FIG. 5C, D).

Autophagic Clearance is Induced in Livers of Vps15 LKO Mice by Fenofibrate Treatment Intrigued by a dramatic amelioration of hepatocyte vacuolation in the livers of Vps15 LKO mice, the inventors have asked whether activated autophagic clearance might be the underlighting mechanism. To test it, the immunoblot of total protein extracts from liver tissue of control and treated with fenofibrate incorporated in food wild-type and Vps15 LKO mice were analyzed with antibodies against lysosomal membrane proteins Lamp1 and Lamp2 as well as autophagy degraded proteins LC3 and p62. As a result, potent accumulation of Lamp and p62 proteins in livers of Vps15 LKO mice was significantly ameliorated by a short-term fenofibrate treatment (FIG. 7). Furthermore, the fenofibrate administration induced an important lipidation of LC3 protein (faster migrating LC3-II form) in livers of both control and Vps15 LKO mice (FIG. 7). Thus, the pharmacological activation of PPARα by fenofibrate promotes autophagic clearance in livers of Vps15 LKO mice.

Fenofibrate and Bezafibrate Treatment Improves Liver Damage of Vps15 LKO Mice

To get further insights into the therapeutic outcomes of fenofibrate treatment in Vps15 LKO mice, the plasma analyses were performed. Consistent with its reported lipid lowering effect, a short-term treatment with fenofibrate incorporated in food was effective in lowering triglyceride levels in the plasma of control mice and resulted in their normalization in Vps15 LKO mice (FIG. 8A). Furthermore, as showed by histological and molecular analyses, the improved liver function in Vps15 LKO mice was reflected by significantly decreased activity of transaminases in plasma of fenofibrate treated mutants (FIGS. 8B and 8C). Finally, the fenofibrate administration in Vps15 LKO mice has significantly decreased the spleen hypertrophy (FIG. 8D). The later shows that fenofibrate administration in Vps15 LKO mice had improved portal hypertension and decreased liver damage as well as inflammation consistent with the histological findings as well as plasma analyses.

To further expand the beneficial effect of fenofibrate in Vps15 LKO mouse model, the inventors have performed the analyses with bezafibrate incorporated in food and fenofibrate administered once a day by oral gavage. These treatments were meant to test: 1) whether different fibrate administered in the same way as fenofibrate and 2) whether administration of the same daily dose of fenofibrate once per day would have similar therapeutic effect. As seen from the biochemical and morphometric analyses presented on FIG. 12, the once-a-day administration of fenofibrate and bezafibrate in food treatment of Vps15 LKO mice had similar therapeutic effect observed with fenofibrate in food treatment. Notably, all three treatment regiments were effective in lowering TG levels (FIG. 12A) and decreasing spleen hypertrophy in Vps15 LKO mice (FIG. 12C). Interestingly, fenofibrate, independently of mode of administration, was more effective in lowering liver damage compared to bezafibrate treatment delivered in this protocol (FIG. 12B). In conclusion, short-term fenofibrate or bezafibrate administration in Vps15 LKO mice is effective as seen from metabolic read-outs and can potently ameliorates liver function.

PPARα is Inhibited in Livers of BA Patients

The inventors findings of the inhibited autophagy and decreased expression of the class 3 PI3K subunits in livers of BA patients and the resemblance of the pathological manifestations in livers of BA patients with the phenotype of Vps15 LKO mice made the inventors hypothesize that PPARα activity might be also inhibited in BA liver tissue. To test it, the immunohistological analyses were performed in the liver tissue biopsies of 7 BA patients and 2 controls. Those have demonstrated that the nuclear localization of PPARα was decreased both in hepatocytes (FIG. 9A1) and in cholangiocytes (FIG. 9A2) and, in turn, PPARα was potently accumulated in cytosol of hepatocytes in liver tissue of BA patients. To get further insights in the status of PPARα transcriptional activity, the transcript levels of its bona fide targets were evaluated by RT-qPCR. Those have shown that consistent with lower nuclear expression of PPARα in livers of BA patients, the expression levels of its known targets such as metabolic enzymes and the proteins involved in fatty acid transport and degradation (AOX, HMGCS2, PEX5, CPT1A, ACADM, HMGCL) as well its novel target in mitochondrial biogenesis that the inventors have recently identified (TFB2M) were significantly downregulated compared to controls (FIGS. 9B1 and 9B2). Notably, the transcript levels of PPARα in livers of BA patients were not different from the controls suggesting that its inhibition occurs at posttranscriptional level (FIG. 9B2). In sum, the inventors show that PPARα transcriptional activity is inhibited in livers of BA patients.

Re-Activation of PPARα with Bezafibrate (BEZA) or Fenofibrate Delivered by Different Protocol (FENO Gavage) is Sufficient for Beneficial Therapeutic Effect in Livers of Vps15 LKO Mice To understand further the molecular mechanisms underlying an improved liver function in Vps15 LKO mice-treated with different fibrate (bezafibrate) administered in the same way as fenofibrate and fenofibrate delivered as once-per day, the additional biochemical, molecular and histological analyses were performed on liver tissue samples of treated mice (FIGS. 10 and 11). Consistent with the initial observations suggesting an improved metabolic status and liver function (FIG. 12) of Vps15 LKO mice, the molecular analyses of mice treated with BEZA (food) and FENO (gavage) demonstrated that both treatments were equally efficient in restoring PPARα transcriptional activity in livers of Vps15 LKO mice as judged by significantly increased transcript levels of PPARα target genes involved in fatty acid transport and degradation (FIG. 10A). These observations at transcript level were further backed by protein expression analyses showing that treatment with both BEZA (food) and FENO (gavage) was equally effective in restoring in livers of Vps15 LKO mice protein expression of PPARα target, a Fabp1 protein (FIG. 10C). Moreover, similar to the fenofibrate treatment delivered in food, both BEZA (food) and FENO (gavage) were effective in reducing the inflammation present in livers of Vps15 LKO mice (FIG. 10A). Notably, the metabolomics analyses in liver tissue of Vps15 LKO mice treated with BEZA (food) and FENO (gavage) further demonstrated that PPARα re-activation was sufficient to restore the metabolic activity such as fatty-acid oxidation in livers of Vps15 mutants. This is evidenced by decreased levels of long-chain fatty acid carnitines and increased levels of short-chain fatty acid carnitines in livers of treated by fibrates Vps15 LKO mice (FIG. 10B). Finally, similar to the effect of treatment with fenofibrate incorporated in food, the administration of BEZA (food) and FENO (gavage) promoted autophagic clearance in livers of Vps15 LKO mice (FIG. 10C). This is supported by observations of decreased Lamp1 and p62 protein levels and increased lipidation of LC3 (LC3-II form) in livers of Vps15 LKO mice treated with BEZA (food) and FENO (gavage) (FIG. 10C). Finally, gross microscopic analyses of liver tissue in Vps15 LKO mice revealed that both short-term treatments with BEZA (food) and FENO (gavage) were sufficient to decrease hepatocyte vacuolation, reduce hepatocyte volume and improve the portal area organization in livers of Vps15 LKO mice (FIG. 11). Therefore, administration of BEZA (food) and FENO (gavage) is similarly efficient to administration of FENO (food) in restoring PPARα transcriptional activity, reducing inflammation and promoting autophagic clearance in livers of Vps15 LKO mice. Altogether, the FENO and BEZA administration ameliorated liver tissue organization of Vps15 LKO mice which is consistent with decreased inflammation and improved metabolic function observed in treated Vps15 mutants.

CONCLUSION

Biliary atresia (BA) is a severe disease of neonates characterized by progressive fibro-obliterative cholangiopathy. It manifests in obstructive bile flow, cholestasis and icterus in neonates. In the face of lack of efficient treatment, the combination of clinical manifestations such as progressive hepatic fibrosis, that culminates in cirrhosis and portal hypertension, leads to liver failure and death of patients by the age of 2 years. Overall, the etiology of cholangiopathies, including BA, represents one of the major knowledge gaps in liver pathophysiology. In order to propose durable therapeutic solutions, there is an urgent need to find a treatment for BA. To this aim, the inventors have combined the molecular analyses of BA patient liver tissue, investigation of genetic mouse model and pre-clinical pharmacological studies.

The present data show that, autophagic degradation is inhibited in the liver tissue of BA patients. Further, defective autophagic lysosomal degradation represents a novel molecular mechanism of BA and is a pathognomonic characteristic of this disease. Second, data show that expression of the class 3 PI3K subunits is severely depleted in liver tissue of a large proportion of BA patients. Third, data show that hepatic manifestation of the liver mutant of the class 3 PI3K, Vps15 LKO mice, mimics the BA and therefore, the Vps15 LKO mice represent a first pre-clinical genetic model of this disease. Forth, data show that PPARα transcriptional activity is inhibited both in livers of BA patients and in livers of Vps15 LKO mice. Finally, data show that a short-term pharmacologic activation of PPARα with fenofibrate and bezafibrate in Vps15 LKO mice significantly improves their liver function advocating its potential use in BA patients. To conclude, data show that BA patients might benefit of pharmacological treatment with synthetic PPARα ligands such as fenofibrate and/or bezafibrate.

REFERENCE

Chardot C, Carton M, Spire-Bendelac N, Le Pommelet C, Gol-mard J L, Auvert B. Epidemiology of biliary atresia in France: anational study 1986-96. J Hepatol 1999; 31:1006-13.

Girard M, Jannot A S, Besnard M, Jacquemin E, Henrion-Caude A. Biliary atresia: does ethnicity matter? J Hepatol 2012; 57:700-1.

Diem H V, Evrard V, Vinh H T, Sokal E M, Janssen M, Otte J B, et al. Pediatric liver transplantation for biliary atresia: results of primary grafts in 328 recipients. Transplantation 2003; 75:1692-7.

Chardot C, Buet C, Serinet M O, Golmard J L, Lachaux A, Roque-laure B, et al. Improving outcomes of biliary atresia: Frenchnational series 1986-2009. J Hepatol 2013; 58:1209-17. Fischler B, Lamireau T. Cholestasis in the newborn and infant. Clin Res Hepatol Gastroenterol 2014; 38:263-7.

Serinet M O, Wildhaber B E, Broue P, Lachaux A, Sarles J, Jacquemin E, et al. Impact of age at Kasai operation on its results in late childhood and adolescence: a rational basis for biliary atresia screening. Pediatrics 2009; 123:1280-6.

Fouquet V, Alves A, Branchereau S, Grabar S, Debray D, Jacquemin E, et al. Long-term outcome of pediatric liver trans-plantation for biliary atresia: a 10-year follow-up in a singlecenter. Liver Transpl 2005; 11:152-60.

Hubscher. What is the long-term outcome of the liver allograft?J Hepatol 2011; 55:702-17. Fischler B, Lamireau T. Cholestasis in the newborn and infant. Clin Res Hepatol Gastroenterol 2014; 38:263-7.

Bezerra J A, Spino C, Magee J C, Shneider B L, Rosenthal P, Wang K S, et al. Use of corticosteroids after hepato-portoenterostomy for bile drainage in infants with biliary atresia: the START randomized clinical trial. JAMA 2014; 311:1750-9.

Willot S, Uhlen S, Michaud L, Briand G, Bonnevalle M, SfeirR, et al. Effect of ursodeoxycholic acid on liver function in children after successful surgery for biliary atresia. Pediatrics 2008; 122:e1236-41.

Davenport M, Parsons C, Tizzard S, Hadzic N. Steroids in biliary atresia: single surgeon, single centre, prospective study. J Hepatol 2013; 59:1054-8.

Chen Y, Nah S A, Chiang L, Krishnaswamy G, Low Y. Postoperative steroid therapy for biliary atresia: systematic review and meta-analysis. J Pediatr Surg 2015; 50:1590-4.

Nizery L, Chardot C, Sissaoui S, Capito C, Henrion-Caude A, Debray D, Girard M et al. Biliary atresia: Clinical advances and perspectives. Clin Res Hepatol Gastroenterol. 2016 June; 40(3):281-287.

The invention claimed is:

1. A method of treatment comprising administering to a patient after hepatoportoenterostomy, an effective amount of a fibrate compound comprising an agonist of the alpha form of PPAR for treatment of biliary atresia.

2. The method according to claim 1, wherein administering the fibrate compound slows progression of biliary atresia in the patient.

3. The method according to claim 1, wherein said agonist of the alpha form of PPAR is not elafibranor.

4. The method according to claim 3, wherein the fibrate compound comprises one or more compounds selected from the group consisting of fenofibrate, ciprofibrate, gemfibrozil, bezafibrate, clinofibrate, clofibrate, clofibride, ronifibrate and simfibrate.

5. The method according to claim 4, wherein the fibrate compound is fenofibrate or bezafibrate.

6. The method according to claim 4, wherein the fibrate compound is a combination of compounds selected from the group consisting of fenofibrate, ciprofibrate, gemfibrozil, bezafibrate, clinofibrate, clofibrate, clofibride, ronifibrate and simfibrate.

7. The method according to claim 4, wherein the fibrate compound is a combination of fenofibrate and bezafibrate.

8. The method according to claim 4, wherein the one or more compounds are formulated separately and co-administered to the subject.

9. The method according to claim 1, said patient being a neonate or an infant.

10. The method according to claim 1, wherein the fibrate compound is administered to the patient once a day.

11. The method according to claim 10, wherein the fibrate compound is administered to the patient before a night fast.

12. The method according to claim 1, said fibrate compound being administered to the patient in the form of a pharmaceutical composition.

13. The method according to claim 1, wherein the fibrate compound is administered to the patient every 12 hours.

14. The method according to claim 1, wherein the amount of the fibrate compound is sufficient to restore an effective autophagic clearance in the patient.

* * * * *